(12) United States Patent
Small-Howard et al.

(10) Patent No.: US 10,857,107 B2
(45) Date of Patent: Dec. 8, 2020

(54) CANNABINOID-CONTAINING COMPLEX MIXTURES FOR THE TREATMENT OF MAST CELL-ASSOCIATED OR BASOPHIL-MEDIATED INFLAMMATORY DISORDERS

(71) Applicant: GBS Global BioPharma, Inc., Ottawa (CA)

(72) Inventors: Andrea Small-Howard, Norwalk, CA (US); Helen Turner, Honolulu, HI (US)

(73) Assignee: GBS Global BioPharma, Inc., Ottawa (CA)

( * ) Notice: Subject to any disclaimer, the term of this patent is extended or adjusted under 35 U.S.C. 154(b) by 0 days.

(21) Appl. No.: 15/885,620

(22) Filed: Jan. 31, 2018

(65) Prior Publication Data

US 2018/0221304 A1   Aug. 9, 2018

Related U.S. Application Data

(60) Provisional application No. 62/453,161, filed on Feb. 1, 2017.

(51) Int. Cl.
*A61K 31/05*   (2006.01)
*A61K 31/352*   (2006.01)
(Continued)

(52) U.S. Cl.
CPC ............ *A61K 31/05* (2013.01); *A61K 31/015* (2013.01); *A61K 31/045* (2013.01);
(Continued)

(58) Field of Classification Search
CPC ........ A61K 31/05; A61K 31/352; A61P 37/00
See application file for complete search history.

(56) References Cited

U.S. PATENT DOCUMENTS 6,949,582 B1 *   9/2005   Wallace ................. A61K 31/05
                                                           514/454
8,673,368 B2    3/2014   Guy et al.
(Continued)

FOREIGN PATENT DOCUMENTS

EP      1189603 A2    3/2002
EP      2037901 B1    3/2009
(Continued)

OTHER PUBLICATIONS

Small-Howard et al, Biochem J. (2005), vol. 388, pp. 465-473. (Year: 2005).*

(Continued)

*Primary Examiner* — Craig D Ricci
*Assistant Examiner* — Janet Coppins
(74) *Attorney, Agent, or Firm* — Fenwick & West LLP

(57) ABSTRACT

Provided herein are cannabinoid-containing complex mixtures suitable for use as active pharmaceutical ingredients. The complex mixtures are comprised of the major cannabinoid, cannabidiol, a first minor cannabinoid, which is cannabigerol, at least a first selected terpene, and optionally a second minor cannabinoid. Also provided are methods of making the complex mixtures, pharmaceutical compositions comprising the complex mixture, and methods of using the pharmaceutical compositions for the treatment of mast cell-related immune disorders, including allergy and atopy (allergic asthma, eczema, rhinitis), mast cell activation syndrome (MCAS), physical and chemical urticarias, idiopathic urticaria, Crohn's disease, inflammatory bowel disorder, dermatitis and contact dermatitis, arthritis and rheumatoid arthritis, canine mastocytosis, and allergy and inflammation in cattle, swine, etc. The methods of the present invention further relate to the treatment of various basophil-mediated immune disorders.

11 Claims, 16 Drawing Sheets

Figure 1:
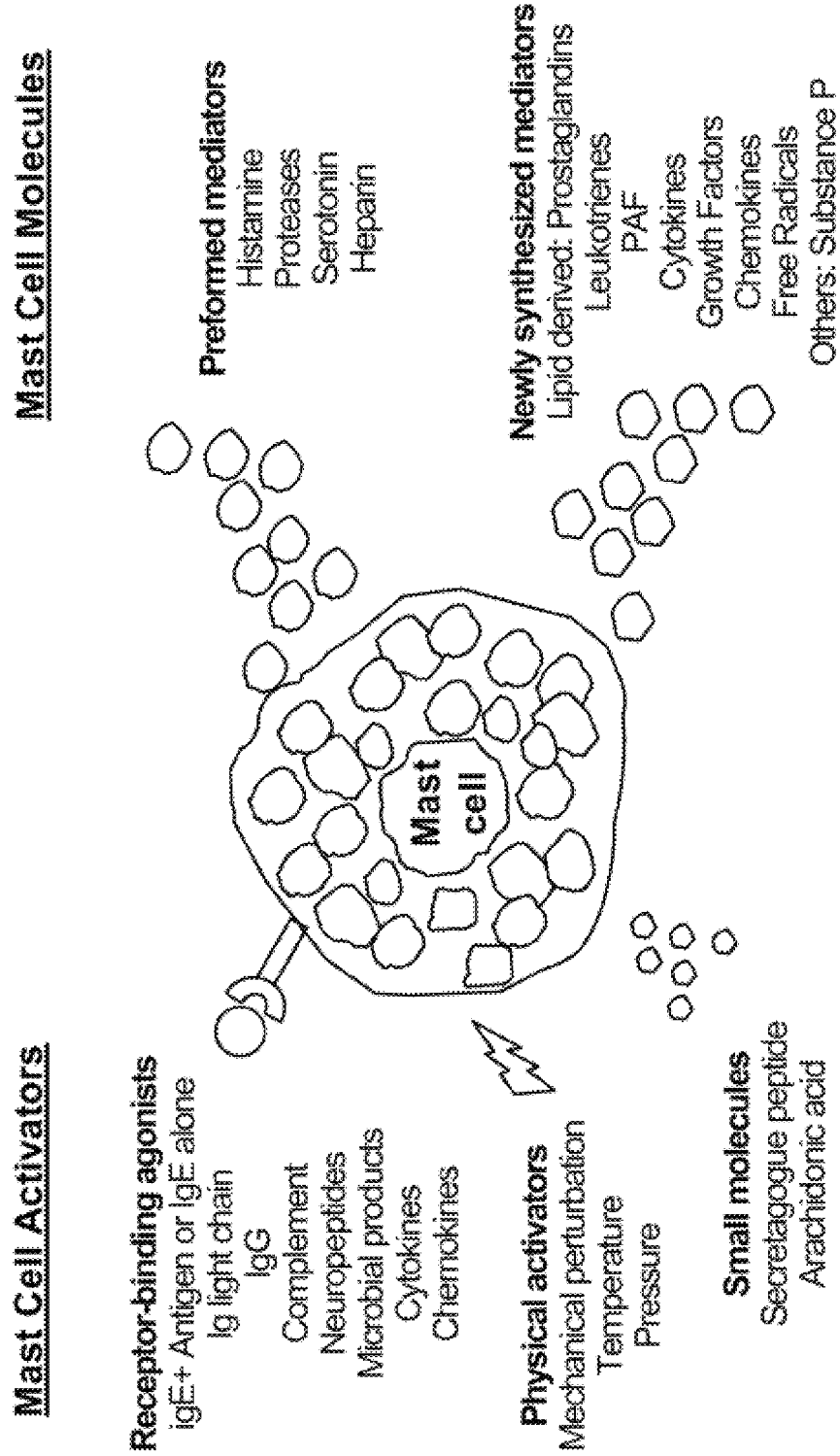

(51) Int. Cl.

| | |
|---|---|
| *A61K 31/355* | (2006.01) |
| *A61P 37/00* | (2006.01) |
| *A61K 36/185* | (2006.01) |
| *A61K 31/015* | (2006.01) |
| *A61P 19/02* | (2006.01) |
| *A61P 37/08* | (2006.01) |
| *A61P 41/00* | (2006.01) |
| *A61P 17/00* | (2006.01) |
| *A61K 31/045* | (2006.01) |
| *A61P 17/04* | (2006.01) |

(52) U.S. Cl.
CPC .......... *A61K 31/352* (2013.01); *A61K 31/355* (2013.01); *A61K 36/185* (2013.01); *A61P 17/00* (2018.01); *A61P 17/04* (2018.01); *A61P 19/02* (2018.01); *A61P 37/00* (2018.01); *A61P 37/08* (2018.01); *A61P 41/00* (2018.01)

(56) References Cited

U.S. PATENT DOCUMENTS

| | | | |
|---|---|---|---|
| 8,758,826 B2* | 6/2014 | Bevier | A61K 47/10 |
| | | | 424/491 |
| 2014/0243405 A1 | 8/2014 | Whalley et al. | |
| 2014/0287068 A1* | 9/2014 | Lewis | A01H 1/04 |
| | | | 424/725 |
| 2015/0343071 A1 | 12/2015 | Vangara et al. | |
| 2016/0039591 A1 | 2/2016 | Kinzer | |
| 2016/0309774 A1* | 10/2016 | Wand | A61K 31/352 |

FOREIGN PATENT DOCUMENTS

| | | |
|---|---|---|
| WO | WO 2007/083098 A1 | 7/2007 |
| WO | WO 2007144628 A1 | 12/2007 |
| WO | WO 2010/127033 A1 | 11/2010 |
| WO | WO 2013/005017 A1 | 1/2013 |
| WO | WO 2013/045891 A1 | 4/2013 |
| WO | WO 2014/202990 A1 | 12/2014 |
| WO | WO 2015/025312 A1 | 2/2015 |
| WO | WO 2015/198078 A1 | 12/2015 |
| WO | WO 2015198071 A1 | 12/2015 |
| WO | WO 2016133824 A1 | 8/2016 |
| WO | WO 2016/138505 A1 | 9/2016 |
| WO | WO 2017/007833 A1 | 1/2017 |
| WO | WO 2017/190249 A1 | 11/2017 |
| WO | WO 2017/192527 A1 | 11/2017 |

OTHER PUBLICATIONS

PCT International Search Report and Written Opinion, PCT Application No. PCT/US2018/016296, dated May 8, 2018, 15 pages.

Samson, M-T. et al. "Differential Roles of CB1 and CB2 Cannabinoid Receptors in Mast Cells," The Journal of Immunology, 2003, pp. 4953-4962, vol. 170.

Nagarkatti, P. et al., "Cannabinoids as Novel Anti-Inflammatory Drugs," Future Med. Chem., Oct. 2009, pp. 1333-1349, vol. 1, No. 7.

Greineisen, W.E. et al., "Immunoactive Effects of Cannabinoids: Considerations for the Therapeutic Use of Cannabinoid Receptor Agonists and Antagonists," Int. Immunopharmacol., May 2010, pp. 547-555, vol. 10, No. 5.

Carrillo-Salinas, F.J. et al., "A Cannabigerol Derivative Suppresses Immune Responses and Protects Mice from Experimental Autoimmune Encephalomyelitis," PLOS One, Apr. 2014, pp. 1-12, vol. 9, Issue 4.

Nadler, M. et al., "Signal Transduction by the High-Affinity Immunoglobulin E Receptor FceRI: Coupling Form to Function," ResearchGate, Advances in Immunology, Feb. 2000, pp. 325-355.

Cascio, M.G. et al., "Evidence That the Plant Cannabinoid Cannabigerol is a Highly Potent $\alpha_2$-Adrenoceptor Agonist and Moderately Potent $5HT_{1A}$ Receptor Antagonist," British Journal of Pharmacology, Jan. 2010, pp. 129-141, vol. 159, No. 1. doi: 10.1111/j.1476-5381.2009.00515.x. Epub Dec. 4, 2009.

Borrelli, F. et al., "Beneficial Effect of the Non-Psychotropic Plant Cannabinoid Cannabigerol on Experimental Inflammatory Bowel Disease," Biochemical Pharmacology, May 2013, pp. 1306-1316, vol. 85, No. 9.

Diaz-Alonso, J. et al., "VCE-003.2, a Novel Cannabigerol Derivative, Enhances Neuronal Progenitor Cell Survival and Alleviates Symptomatology in Murine Models of Huntington's Disease," Scientific Reports, Jul. 19, 2016, pp. 1-15, vol. 6, No. 29789.

Pagano, E. et al., "Effect of Non-Psychotropic Plant-Derived Cannabinoids on Bladder Contractility: Focus on Cannabigerol," ResearchGate, Natural Product Communications, 2015, pp. 1009-1012, vol. 10, No. 6.

Sohn, J-W. et al., "Neuronal Circuits That Regulate Feeding Behavior and Metabolism," Trends in Neurosciences, Sep. 2013, pp. 504-512, vol. 36, No. 9.

Small-Howard, A.L. et al., "Anti-Inflammatory Potential of CB1-Mediated cAMP Elevation in Mast Cells," Biochem. J., 2005, pp. 465-473, vol. 388.

Kuehn, H.S. et al., "G Protein-Coupled Receptors and the Modification of $F_{C\epsilon}RI$-Mediated Mast Cell Activation," Immunol Lett., Nov. 15, 2007, pp. 59-69, vol. 113, No. 2.

Weston, M.C. et al., "Effects of Phosphodiesterase Inhibitors on Human Lung Mast Cell and Basophil Function," British Journal of Pharmacology, May 1997, pp. 287-295, vol. 121, No. 2.

Penner, R., "Multiple Signaling Pathways Control Stimulus-Secretion Coupling in Rat Peritoneal Mast Cells," Proc. Natl. Acad. Sci., Dec. 1988, pp. 9856-9860, vol. 85.

Weston, M.C. et al., "Regulation of Human Mast Cell and Basophil Function by cAMP," Gen. Pharmac., 1998, pp. 715-719, vol. 31, No. 5.

* cited by examiner

FIG. 9 percentage inhibition of FcepsilonR1 induced mast cell degranulation

- ENT 2 predicted
- ENT 2 actual

FIG. 10

|  | ENT1 | ENT2 | ENT3 | ENT4 | ENT5 | ENT6 | ENT7 | ENT8 | ENT9 | ENT10 | ENT11 | ENT12 |
|---|---|---|---|---|---|---|---|---|---|---|---|---|
| Cannabidiol | 23 |  | 23 | 23 | 23 | 23 | 23 | 23 | 23 | 23 | 23 | 23 |
| Cannabichromene | 0 |  | 0 | 0 |  |  | 0 | 0 |  | 0 | 0 | 0 |
| Cannabigerol | 4 |  | 4 |  | 4 |  | 4 |  | 4 | 4 | 4 | 4 |
| Cannabidivarin | -26 |  | -26 |  |  | -26 |  | -26 | -26 | -26 | -26 | -26 |
| Limonene | 24 | 24 |  | 24 | 24 | 24 |  |  | 24 | 24 |  |  |
| Linalool | 2 | 2 |  | 2 | 2 | 2 |  |  | 2 | 2 |  |  |
| Nerolidol | -1 | -1 |  | -1 | -1 | -1 |  |  | -1 |  | -1 |  |
| Pinene | -3 | -3 |  | -3 | -3 | -3 |  | -3 | -3 |  |  | -3 |
| Phytol | 1 | 1 |  | 1 | 1 | 1 |  |  | 1 |  |  | 1 |
| Predicted additive | 24 | 23 | 1 | 46 | 50 | 20 | 27 | -3 | 24 | 27 | 0 | -1 |
| Actual | 82 | 55 | 43 | 24 | 62 | 3 | 46 | 4 | 61 | 63 | 28 | 31 |
| Fold increase actual performance over predicted additive | 3.4 | 2.4 | 43.0 | 0.5 | 1.2 | 0.2 | 1.7 | (>1.3) | 2.5 | 2.3 | (>28) | (>30) |

FIG. 11

| | ENT6 | ENT9 |
|---|---|---|
| Cannabidiol | 23 | 23 |
| Cannabichromene | | |
| Cannabigerol | | 4 |
| Cannabidivarin | -26 | -26 |
| Limonene | 24 | 24 |
| Linalool | 2 | 2 |
| Nerolidol | -1 | -1 |
| Pinene | -3 | -3 |
| Phytol | 1 | 1 |
| Predicted additive | 20 | 24 |
| Actual | 3 | 61 |

| | ENT8 | ENT9 |
|---|---|---|
| | 23 | 23 |
| | 0 | |
| | | 4 |
| | -26 | -26 |
| | | 24 |
| | | 2 |
| | | -1 |
| | -3 | -3 |
| | | 1 |
| | -3 | 24 |
| | 4 | 61 |

FIG. 15

| | LTC4 release (pg/30 million cells) at 250ng/ml DNP-BSA | % release | %inhibiton |
|---|---|---|---|
| Negative Control | 146 | 100 | 0 |
| ENT1A | 39 | 27% | 73 |
| ENT2 | 135 | 92% | 8 |
| ENT3A | 74 | 51% | 49 |
| ENT8A | 71 | 49% | 51 |
| ENT9A | 69 | 47% | 53 |

CANNABINOID-CONTAINING COMPLEX MIXTURES FOR THE TREATMENT OF MAST CELL-ASSOCIATED OR BASOPHIL-MEDIATED INFLAMMATORY DISORDERS

1. CROSS REFERENCE TO RELATED APPLICATIONS

This application claims the benefit of U.S. Provisional Application No. 62/453,161, filed Feb. 1, 2017, which is hereby incorporated in its entirety by reference.

2. BACKGROUND

Inflammatory responses can be physiologically and patho-physiologically beneficial, because inflammatory responses are required for wound healing, and resolution and regression of viral or bacterial infections. However, hyper-inflammatory responses can be harmful because they relate to allergic responses or anaphylactoid, anaphylactic or idiopathic inflammations. Mast cells are central to the initiation, and maintenance, of inflammation.

Mast cells are strategically located within the body: they reside close to blood vessels, nerves and lymphatic ducts in tissues that interface with the external environment (e.g. airways, GI tract, uterus, skin). In response to a variety of stimuli including challenges to innate and acquired immunity, CNS derived agents, and physical stressors, mast cells initiate inflammatory site formation through three coupled sets of events: (1) release of pre-formed cytoplasmic granules containing pro-inflammatory mediators such as histamine ('degranulation'), (2) de novo biosynthesis of bioactive lipid mediators such as leukotrienes and prostaglandins, and (3) de novo transcriptional activation of the genes for a range of cytokines, chemokines and growth factors. Mast cell activation results in the establishment of an inflammatory site, classically characterized by rubor (reddening due to vasodilation), tumor (swelling due to edema), calor (heat due to intense metabolic activity of infiltrating leukocytes and increased blood flow), dolor (pain caused by mediator effects on local sensory nerve endings) and tissue remodeling/repair events including angiogenesis, fibroplasia and epithelial proliferation, which are initiated by the matrix-active proteases secreted during degranulation.

Basophils are another type of granulocyte, having similar functions and characteristics as mast cells. Basophils are also responsible for inflammatory reactions in immune responses. When activated, they degranulate to release histamine, proteoglycans such as heparin and chondroitin, and proteases such as elastase and lysophospholipase. They also secret lipid mediators such as leukotrienes and various cytokines. Mast cells and basophils share a number of common activation pathways, signaling mechanisms and functional outputs.

The centrality of mast cells and basophils to inflammation, the large number of inflammatory disorders in which these cells have been implicated, and the wide range of stimuli which have been shown to initiate mast cell or basophil responses, have established these immune cells as priority strategic targets in developing new anti-inflammatory therapies. In particular, strategies that simultaneously inhibit multiple arms of the mast cell (or basophil) response (enumerated as (1), (2), (3) above) or inhibit signaling pathways that are common to initiating all arms of the response, are likely to be superior to currently available anti-histamines (which leave bioactive lipid and cytokine synthesis pathways intact), NSAIDs (which target synthetic enzymes for leukotrienes and prostaglandins), or monoclonal antibody therapies/receptor blockers that solely target cytokine pathways. This parallel targeting of multiple pathways is likely to require expertly-designed combinatorial mixtures of compounds that are not currently available or experimentally proven to be effective in controlled tests.

Traditional medicine from many cultures suggests that plants are possible sources of complex chemical mixtures that can be used to treat diverse human conditions, including inflammation. For example, compounds found in *Cannabis sativa* L. have been suggested to be involved in regulating immune responses. A range of endogenous cannabinoids (the endo-cannabinoids) secreted from neural, epithelial and immune tissues regulate a vast range of physiological processes, including immunity, and there are metabotropic and ionotropic receptors for these endocannabinoids on a variety of immune system cells, including mast cells. Similarly, some terpenes have been suggested to have anti-inflammatory potential, and the signaling pathways that they target are present in immune cells such as mast cells.

However, safety, efficacy and consistency of plant-derived medicines do not yet approach traditional pharmaceutical standards for widespread therapeutic deployment. Thus, there is a need for well-defined compositions of cannabinoids and terpenes that selectively exert anti-inflammatory effects, especially on mast cells and basophils, in order to develop effective anti-inflammatory therapeutics.

3. SUMMARY

The present invention provides novel cannabinoid-containing complex mixtures suitable for use as active pharmaceutical ingredients, methods of making the complex mixtures, and pharmaceutical compositions comprising the complex mixtures. The invention further relates to methods of their use for the treatment and prevention of chronic and acute inflammatory disorders in mammals, including mast cell or basophil-mediated inflammatory disorders.

Cannabinoid-containing complex mixtures of the present invention are mixtures comprising a plurality of compounds identified from *Cannabis* spp., broadly divided into three groups: (a) major cannabinoids, which are highly abundant in the plant, (b) minor cannabinoids, and (c) terpenes. The concentrations of these compounds in the plant vary widely across *Cannabis* strains, cultivars, time, cultivation methods and environmental conditions, etc.

While major cannabinoids have been extensively studied, minor cannabinoids and terpenes are less well studied and the medical potential of bespoke mixtures that cross these categories has not been fully explored. Moreover, the complexity of plant-derived mixtures encompasses compounds which are likely to act additively, synergistically or oppositionally on a given target signaling pathway. The latter means that translation from plant to clinic is not straightforward, and underscores the need for deconstruction, optimization and reconstruction of mixtures of therapeutically desirable composition. The present invention meets the need by providing the methods for identifying the therapeutically desirable composition by deconstruction, optimization and reconstruction processes as well as the composition identified by the methods.

Cannabinoid-containing complex mixtures disclosed herein provide novel methods for treating and preventing various diseases involving hyper-inflammatory responses, by suppressing both mast cell degranulation and bioactive lipid release (FIG. 1). These methods can be effective in treating and preventing various inflammatory disorders involving mast cells. Such inflammatory disorders include, but are not limited to, allergy and atopy (allergic asthma, eczema, rhinitis), mast cell activation syndrome (MCAS), physical and chemical urticarias, idiopathic urticaria, Crohn's disease, inflammatory bowel disorder, dermatitis and contact dermatitis, arthritis and rheumatoid arthritis, a dermal, tissue or systemic response to a sting, or other anaphylactic or anaphylactoid stimulus, canine mastocytosis, and allergy and inflammation in cattle, swine, etc.

The novel compositions and methods of the present invention are expected to replace or supplement other anti-inflammatory approaches available in the art, which are still imperfect as follows:

First, the co-targeting of at least two arms of the mast cell activation process improves over current approaches as described above.

Second, extant chronic anti-inflammatory approaches using corticosteroids are subject to side-effects and desensitization, and monoclonal antibody therapies that target TNFα, etc., have considerable side effect profiles and are expensive. In contrast, anecdotal evidence and patient reported outcomes from the large number of current marijuana users in the population (both medicinal and recreational) suggest (1) low side effect profiles and (2) long term efficacy without significant desensitization.

Third, in blocking degranulation, the effects of the mixtures described here have ancillary effects on mediators other than histamine, but which are also contained within mast cell granules. These include, but are not limited to, serotonin, tissue-active peptides, granins and the large family of mast cell proteases ("MCPT") such as chymase and tryptase which are highly active in vasodilation and tissue remodeling.

The novel compositions and methods of the present invention are expected to replace or supplement current usage modalities for marijuana-based medicines available in the art, which are still imperfect, as follows:

First, the method 'homes in' on desirable compositions of cannabinoids/terpenes for anti-inflammatory therapy, which could later be presented either in bespoke synthetic compositions or in judging/ranking the merits of certain naturally occurring Cannabis strains/cultivars for therapeutic applications, which is an improvement over current prescribing or strain selection methodologies which are based largely on anecdotal evidence.

Second, the method provides for the design of synthetic compositions which can be manufactured consistently and in a contaminant free manner, which is an improvement over the current state of the medical marijuana production process where batch-to-batch consistency is not assured (due to differences in growing conditions, genetic/epigenetic and metabolic variance between plants and variations in extraction methods) and where microbial and chemical contamination is a persistent issue.

Third, the bespoke mixtures presented here are free of or substantially free of the major psychoactive cannabinoid, delta-9 tetrahydrocannabinol (THC). These mixtures therefore present a decreased regulatory and ethical burden when compared to medical marijuana as it is commonly available.

Accordingly, the present invention has great value for the treatment and prevention of various inflammatory diseases.

One aspect of the present invention relates to a pharmaceutically active ingredient comprising cannabidiol (CBD), cannabigerol (CBG) as a first minor cannabinoid, at least a first selected terpene, and optionally a second minor cannabinoid.

In some embodiments, the pharmaceutically active ingredient further comprises a second minor cannabinoid. In some embodiments, the second minor cannabinoid is cannabichromene (CBC). In some embodiments, the second minor cannabinoid is cannabidivarin (CBV).

In some embodiments, the pharmaceutically active ingredient further comprises a third minor cannabinoid. In some embodiments, the second and the third minor cannabinoid are cannabichromene (CBC) and cannabidivarin (CBV), respectively.

In some embodiments, the first selected terpene is limonene. In some embodiments, the first selected terpene is linalool.

In some embodiments, the pharmaceutically active ingredient further comprises a second selected terpene. In some embodiments, the second selected terpene is limonene. In some embodiments, the second selected terpene is linalool. In some embodiments, the first and the second selected terpene are limonene and linalool.

In some embodiments, the pharmaceutically active ingredient comprises lirnonene, linalool, nerolidol, pinene, and phytol.

In some embodiments, the pharmaceutically active ingredient is substantially free of delta-9, THC.

In some embodiments, cannabidiol (CBD), the minor cannabinoids, and the selected terpenes collectively constitute at least 75% by weight of the pharmaceutically active ingredient. In some embodiments, cannabidiol (CBD), the minor cannabinoids, and the selected terpenes collectively constitute at least 80, 85, 90, or 95% by weight of the pharmaceutically active ingredient.

In some embodiments, all compounds in the pharmaceutically active ingredient other than the cannabidiol (CBD), the minor cannabinoids, and the selected terpenes are extractable from *Cannabis sativa*.

In some embodiments, cannabidiol (CBD) constitutes 7-25%, the minor cannabinoids collectively constitute 15-65%, and the selected terpenes collectively constitute 13-65% by weight of the pharmaceutically active ingredient.

In some embodiments, cannabidiol (CBD) constitutes 15-25%, the minor cannabinoids collectively constitute 15-65%, and the selected terpenes collectively constitute 18-65% by weight of the pharmaceutically active ingredient.

In another aspect, methods are provided for making a pharmaceutically active ingredient, comprising steps, in any order, of mixing: cannabidiol (CBD); cannabigerol (CBG) as a first minor cannabinoid; at least a first selected terpene; and optionally, a second minor cannabinoid.

In some embodiments, at least one of cannabidiol, the first minor cannabinoid, the first selected terpene and the optional second minor cannabinoid are added to a *Cannabis sativa* extract.

In some embodiments, the method further comprises a preceding step of measuring the concentration in the *Cannabis sativa* extract of cannabidiol, the first minor cannabinoid, and the first selected terpene.

In some embodiments, the at least one of cannabidiol, the first minor cannabinoid, and the first selected terpene are added to achieve a predetermined concentration in the pharmaceutically active ingredient.

In some embodiments, the method further comprises a preceding step of preparing the *Cannabis sativa* extract. In some embodiments, the *Cannabis sativa* extract is prepared from a *Cannabis sativa* strain selected to best approximate the predetermined composition of the active ingredient.

Some embodiments of the present invention are related to a pharmaceutically active ingredient produced by the method provided herein.

Some embodiments of the present invention are directed to a pharmaceutical composition comprising the pharmaceutically active ingredient provided herein and pharmaceutically acceptable carrier or diluent.

In some embodiments, the pharmaceutical composition is in an oil, an emulsion, a gel, or an aerosol.

In some embodiments, the pharmaceutical composition is formulated for administration by inhalation, by vaporizer, by nebulizer, or by aerosolizer. In some embodiments, the pharmaceutical composition is formulated for oral administration, for buccal administration or for sublingual administration. In some embodiments, the pharmaceutical composition is formulated for intravenous, intramuscular, or subcutaneous administration. In some embodiments, the pharmaceutical composition is formulated for intrathecal or intracerebroventricular administration. In some embodiments, the pharmaceutical composition is formulated for topical administration.

In some embodiments, the pharmaceutically active ingredient is present in the pharmaceutical composition at a concentration of of at least 0.01, 0.1, 0.5, or 1 mg/ml.

In another aspect, methods of treating disorders of the immune system are provided, the methods comprising administering an effective amount of the pharmaceutical composition disclosed herein.

In some embodiments, the disorder of the immune system is allergy or atopy. In some embodiments, the disorder of the immune system is Mast Cell Activation Syndrome ("MCAS"), physical and chemical urticarias, idiopathic urticaria, Crohn's Disease, inflammatory bowel disease, dermatitis and contact dermatitis, arthritis, canine mastocytosis, or allergy or inflammation in a non-human animal. In some embodiments the disorder is a dermal, tissue or systemic response to a sting, or other anaphylactic or anaphylactoid stimulus.

In some embodiments, the immune disorder is a disease involving dysregulation of CB1 or CB2 receptor, or cAMP of mast cells. In some embodiments, the immune disorder is a disease involving hyper-activation of CB1 or CB2 receptor or suppression of cAMP of mast cells.

In some embodiments, the disorder of the immune system is a disease involving dysregulation of one or more mast cell mediators. In some embodiments, the mast cell mediators are preformed mediators or newly synthesized mediators. In some embodiments, the mast cell mediators are preformed mediators selected from the group consisting of histamine, mast cell proteases including, but not limited to, chymase and tryptase, serotonin, and heparin. In some embodiments, the mast cell mediators are newly synthesized mediators selected from the group consisting of bioactive lipids (including but not limited to prostaglandins and leukotrienes), PAF, cytokines, growth factors, chemokines, free radicals, and Substance P.

In some embodiments, the disorder of the immune system is a disease involving dysregulation of one or more basophil mediators.

In some embodiments, the disorder of the immune system is a disease involving hyper-activation of mast cells. In some embodiments, the hyper-activation of the mast cells is by a receptor-binding agonist selected from the group consisting of IgE+Antigen, Ig G, IgE, Ig light chain, Complement, Neuropeptides, Microbial products, Cytokines, and Chemokines. In some embodiments, the hyper-activation of the mast cells is by mechanical perturbation, temperature or pressure. In some embodiments, the hyper-activation of the mast cells is by small molecules selected from the group consisting of secretagogues (including but not limited to insect-derived venom peptides) or arachidonic acid metabolites.

In some embodiments, the disorder of the immune system is a disease involving hyper-activation of basophils.

In some embodiments, the disorder of the immune system is a disease involving abnormal degranulation of mast cells. In some embodiments, the disorder of the immune system is a disease involving abnormal synthesis of bioactive lipid mediators.

In some embodiments, the disorder of the immune system is a disease involving abnormal degranulation of basophils.

In some embodiments, the pharmaceutical composition is administered by inhalation. In some embodiments, the pharmaceutical composition is administered orally. In some embodiments, the pharmaceutical composition is administered by buccal administration. In some embodiments, the pharmaceutical composition is delivered by sublingual administration. In some embodiments, the pharmaceutical composition is administered by injection. In some embodiments, the pharmaceutical composition is administered by topical application.

In some embodiments, the pharmaceutical composition is administered in an amount sufficient to suppress histamine secretion via degranulation of secretory granules from mast cells. In some embodiments, the pharmaceutical composition is administered in an amount sufficient to suppress bioactive lipid release or the production of pro-inflammatory cytokines, chemokines or growth factors from mast cells.

In some embodiments, the cannabidiol is administered in an amount of less than 1 g per dose. In some embodiments, the cannabidiol is administered in an amount of less than 500 mg per dose. In some embodiments, the cannabidiol is administered in an amount of less than 100 mg per dose. In some embodiments, the cannabidiol is administered in an amount of less than 10 mg per dose.

In some embodiments, the pharmaceutical composition is administered p.r.n. In some embodiments, the pharmaceutical composition is administered once a day. In some embodiments, the pharmaceutical composition is administered 2-4 times a day. In some embodiments, the pharmaceutical composition is administered 2-4 times a week. In some embodiments, the pharmaceutical composition is administered once a week. In some embodiments, the pharmaceutical composition is administered once every two weeks.

These and other aspects of the invention are described in further detail below.

4. BRIEF DESCRIPTION OF THE DRAWINGS

FIG. 1 illustrates various mast cell activators (left), including receptor-binding agonists, physical activators and small molecules, and various mast cell molecules (right), including preformed mediators and newly synthesized mediators. This figure is modified from Silver and Curley, Trends in Neurosciences 36:9, 513-521 (2013), available at http://www.cell.com/trends/neurosciences/fulltext/S0166-2236(13)00112-4.

Figure 2:
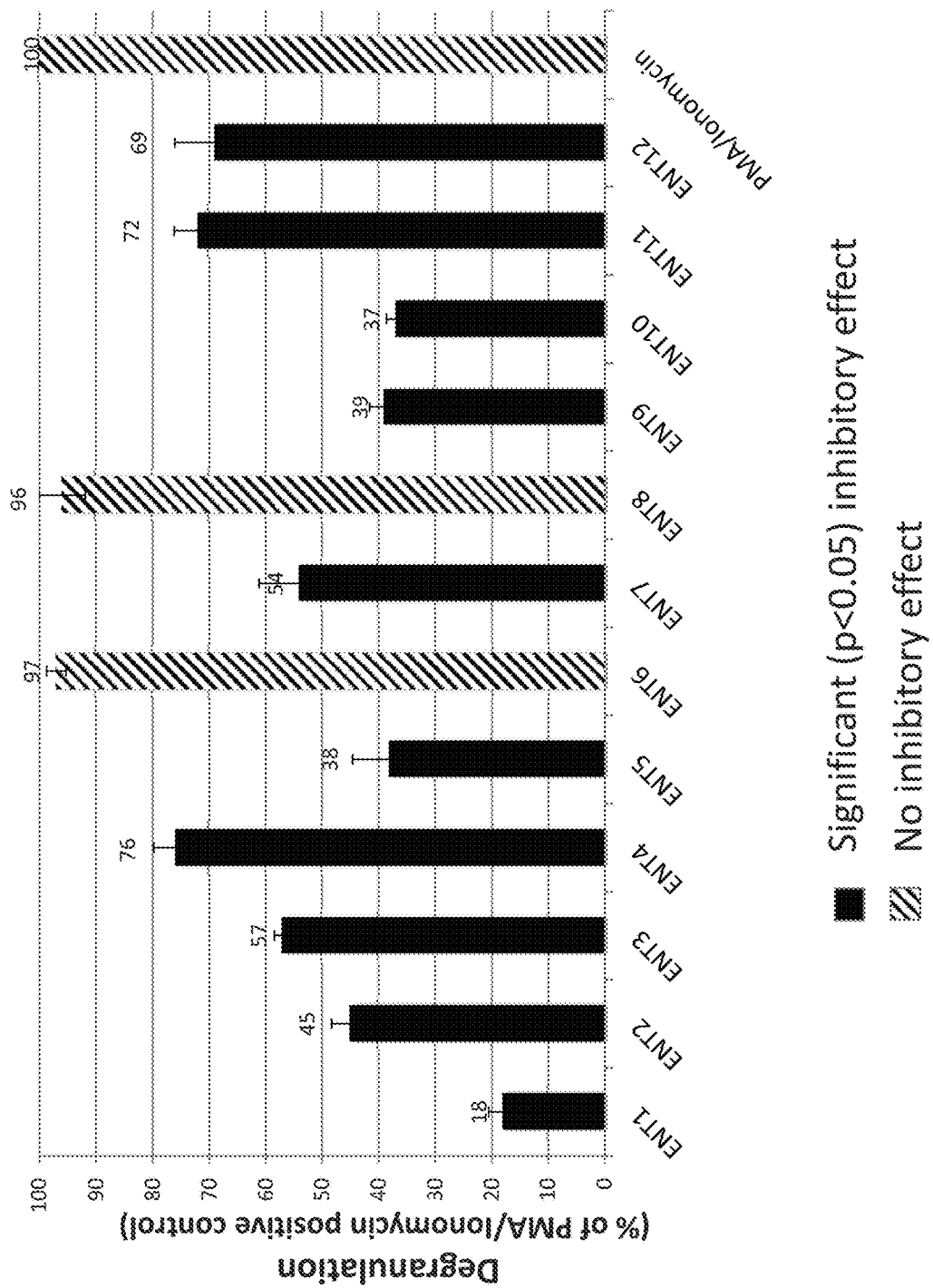

FIG. 2 provides data from Example 2, illustrating FcεRI-induced mast cell degranulation measured by histamine release in the presence of various cannabinoid-containing complex mixtures comprising cannabidiol and one of twelve sub-mixtures (ENT 1-ENT12). The Y-axis shows % degranulation compared to degranulation in the presence of PMA/Ionomycin (maximal degranulation, 100%). Cannabinoid-containing complex mixtures with significant inhibitory effects on degranulation (p<0.05) are presented with solid bars and complex mixtures without significant inhibitory effects on degranulation are presented with cross-hatched bars.

FIG. 3A tabulates % degranulation (% secretion) presented in FIG. 2 (second column), rank order of % degranulation (% secretion) (third column), % inhibition of degranulation calculated by subtracting the % inhibition of degranulation from 100% (fourth column), and rank order of % inhibition of degranulation (fifth column). FIG. 3B provides a box and whisker plot summarizing distribution of % inhibition of FcεRI-induced mast cell degranulation by the cannabinoid-containing complex mixtures presented in FIG. 3A.

Figure 4:
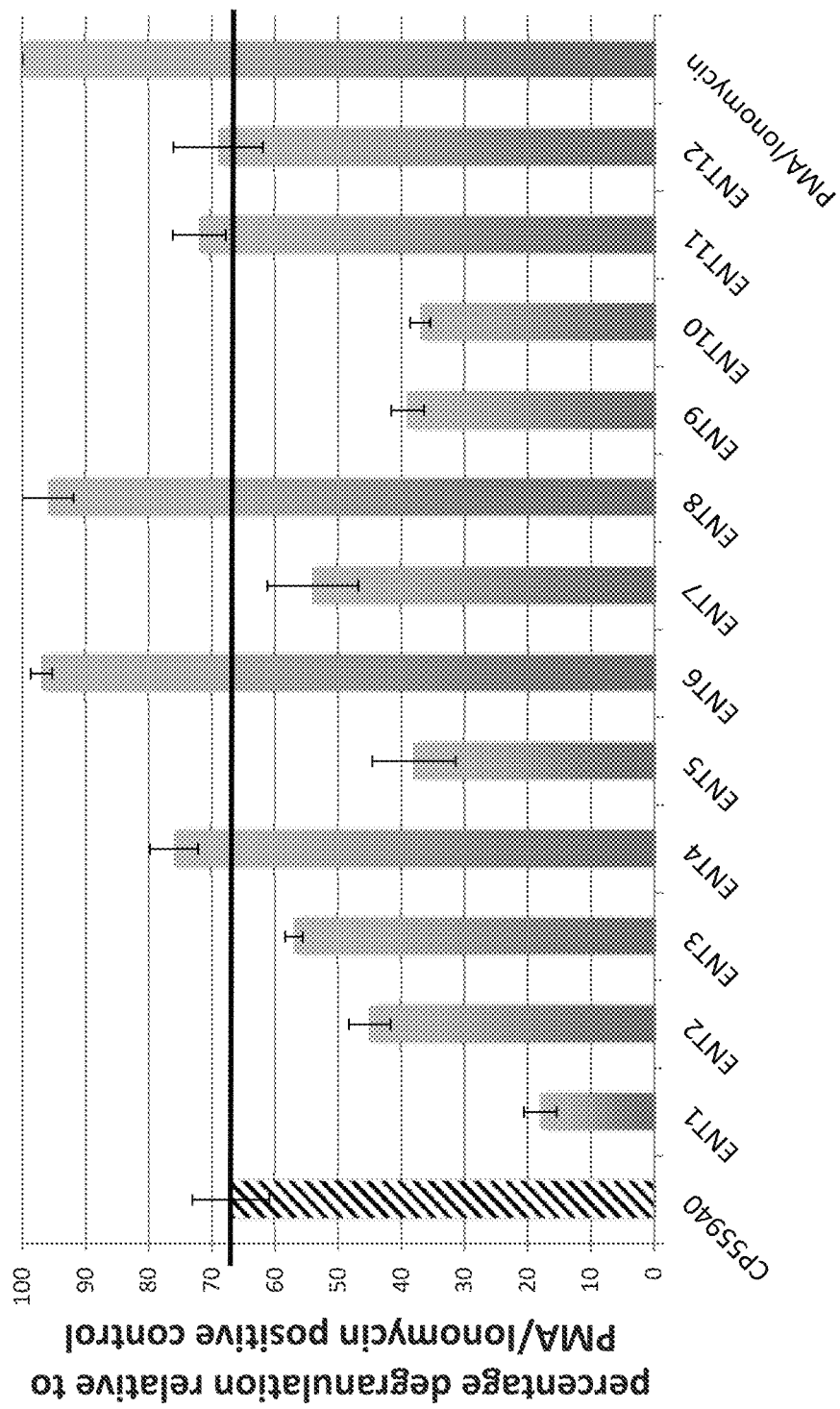

FIG. 4 provides a bar graph illustrating % mast cell degranulation in the presence of various cannabinoid-containing complex mixtures or in the presence of the delta-9 tetrahydrocannabinol (THC) mimetic, CP55940 (cross-hatched bar). A horizontal line is drawn across the bar graph to compare inhibitory effects on degranulation by CP55930 with inhibitory effects of various cannabinoid-containing complex mixtures.

Figure 5:
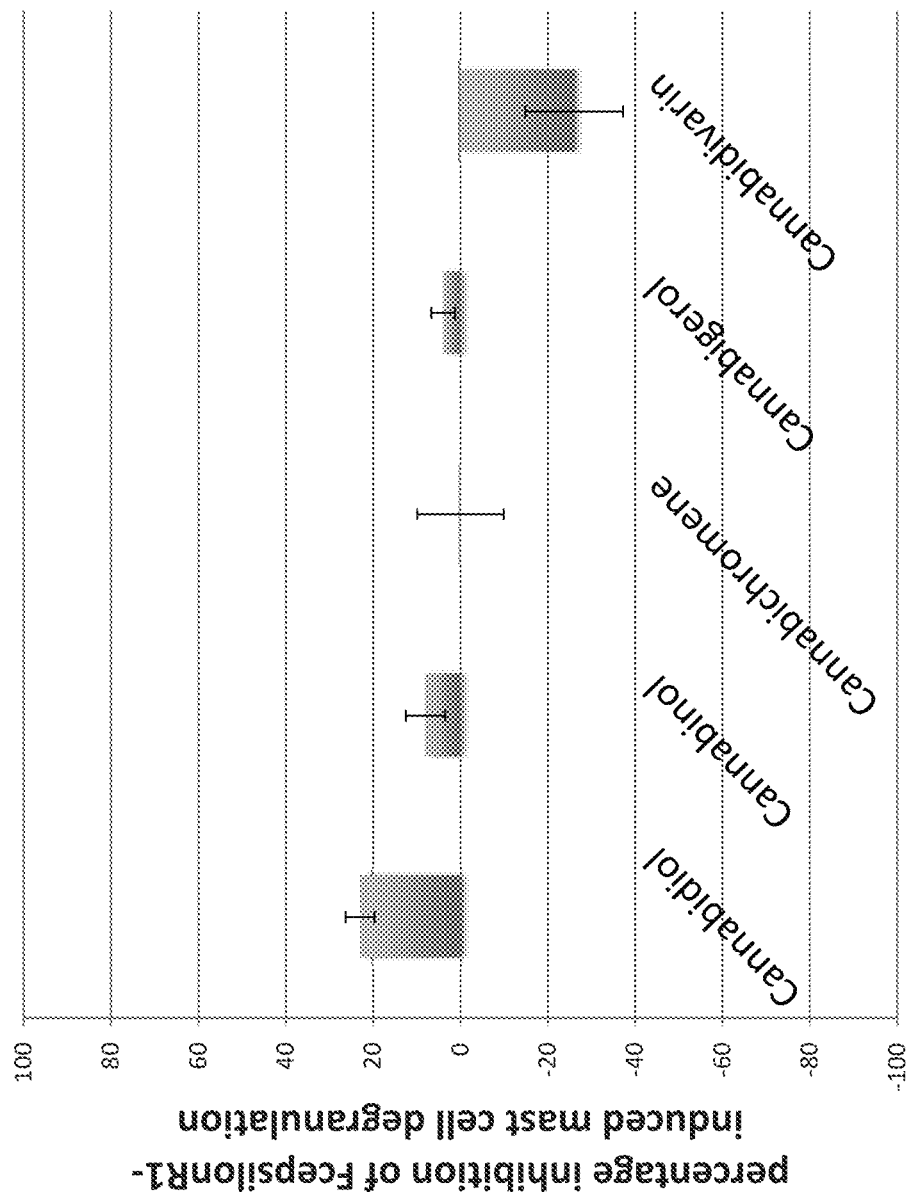

FIG. 5 is a bar graph presenting data from Example 3 illustrating % inhibition of FcεRI-induced mast cell degranulation by cannabidiol (CBD), cannabinol (CBN), cannabichromene (CBC), cannabigerol (CBG) or cannabidivarin (CBV) individually.

Figure 6:
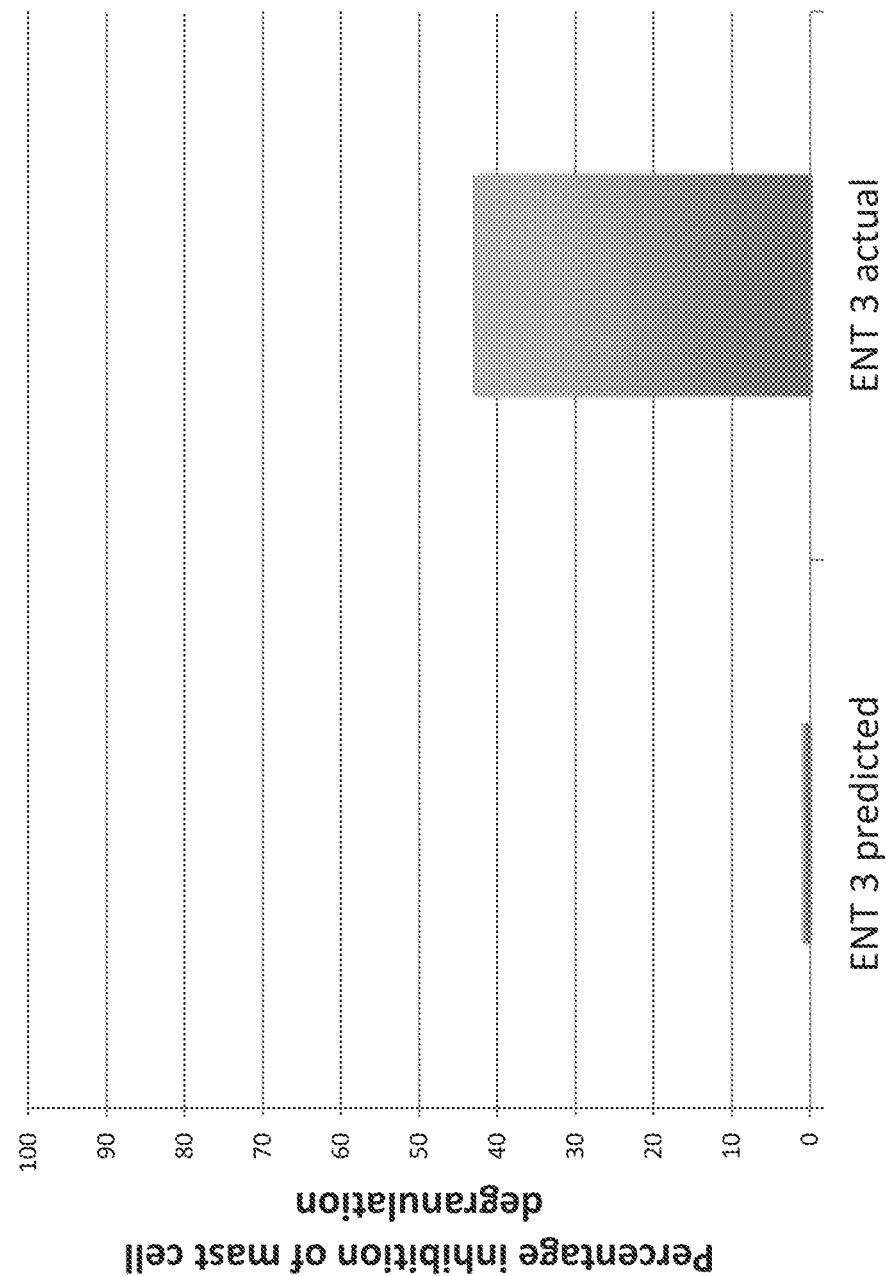

FIG. 6 compares a predicted % inhibition of FcεRI-induced degranulation by a cannabinoid-containing complex mixture comprising cannabidiol and ENT 3 (left) and an actual % inhibition by the complex mixture. The inhibitory effects were predicted by summing % inhibition of FcεRI-induced degranulation by individual components of the complex mixture.

Figure 7B:
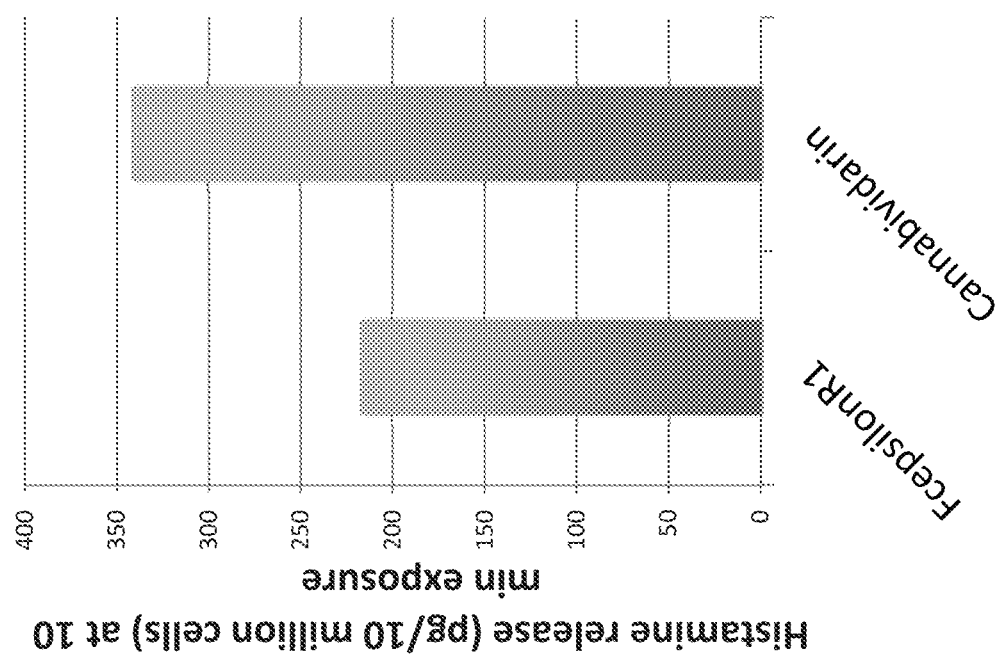
Figure 7A:
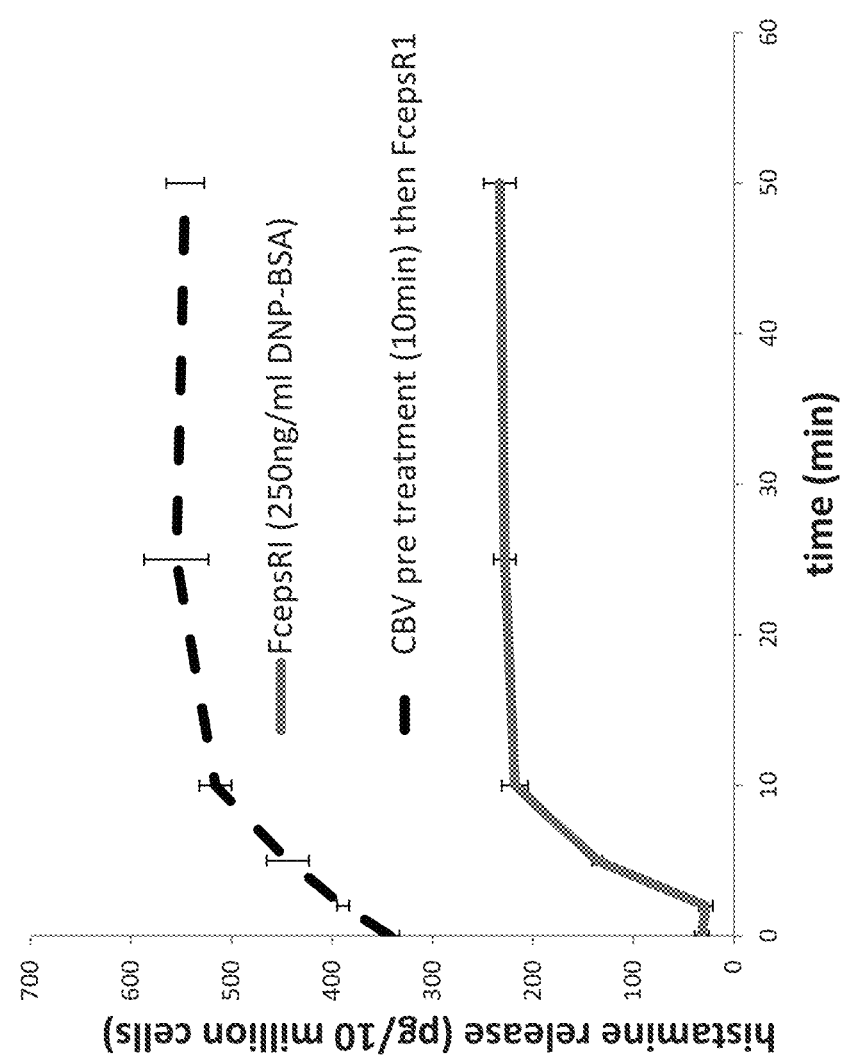

FIG. 7A provides data from Example 3 illustrating pro-inflammatory effects of cannabidivarin. The graph shows time-course of FcεRI-induced histamine release in control mast cells (solid line) and mast cells pretreated with cannabidivarin for 10 minutes (dashed line). The X-axis represents minutes after application of the FcεRI crosslinking agonist, and the y-axis represents the amount of histamine release (pg/10 million cells). FIG. 7B compares histamine release (pg/10 million cells) measured 10 minutes after exposure to the FcεRI crosslinking agonist (left) or to cannabidivarin without the FcεRI crosslinking agonist (right).

Figure 8:
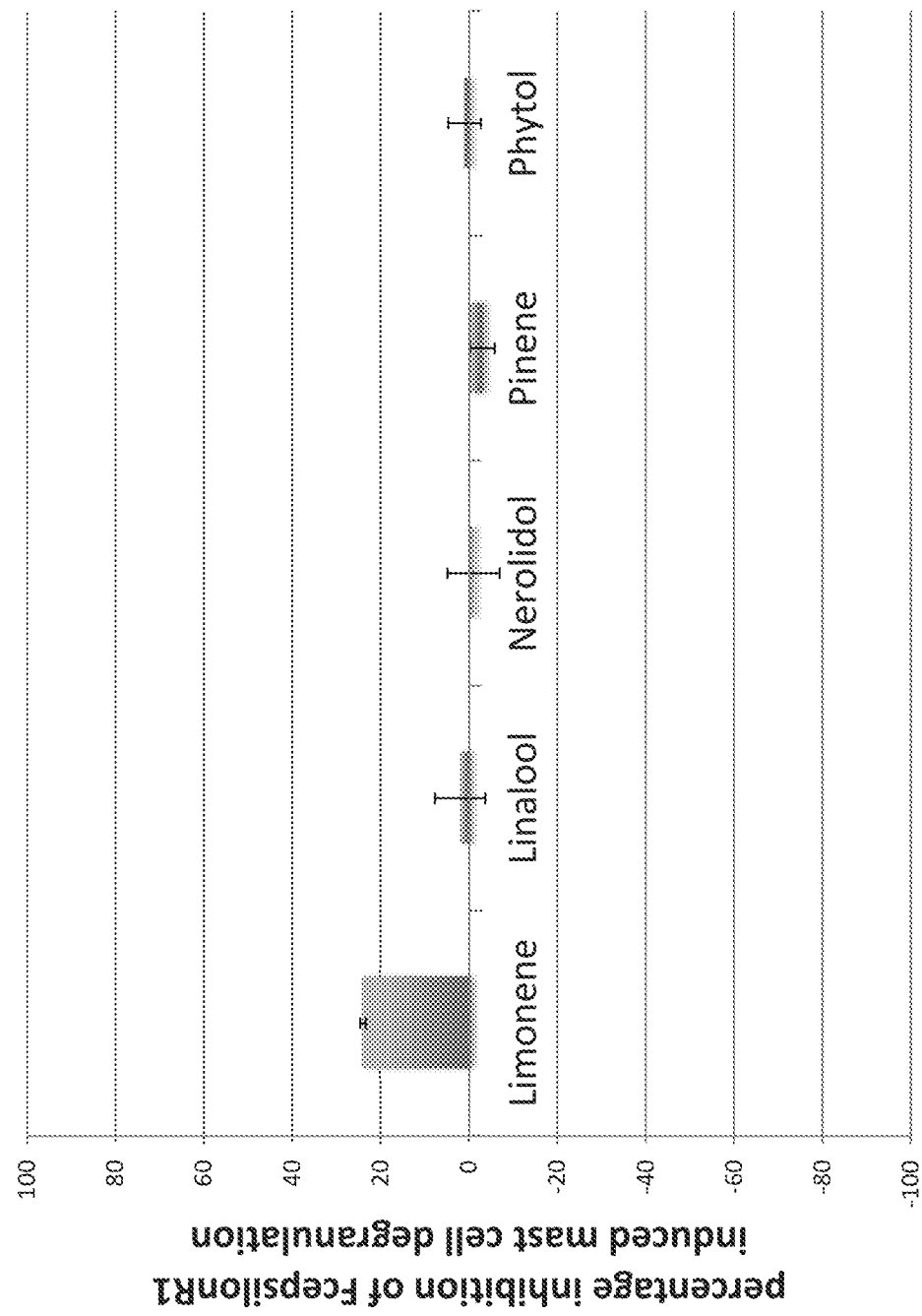

FIG. 8 shows a bar graph presenting data from Example 3 illustrating % inhibition of FcεRI-induced mast cell degranulation by each of 5 individual terpenes: limonene, linalool, nerolidol, pinene, and phytol.

FIG. 9 compares predicted % inhibition of FcεRI-induced degranulation by a cannabinoid-containing complex mixture comprising cannabidiol (CBD) and ENT 2 (left) to the actual % inhibition observed with the complex mixture. The inhibitory effects were predicted by summing % inhibition of FcεRI-induced degranulation by individual components of the complex mixture.

FIG. 10 provides predicted % inhibition of FcεRI-induced degranulation by a cannabinoid-containing complex mixture comprising cannabidiol and one of the twelve sub-mixtures (ENT 1-ENT12) (row labeled "predicted additive") and actual % inhibition by the complex mixtures (row labeled "actual"). The row labeled "Fold increase actual performance over predicted" shows ratios between predicted values and actual values. Predicted values were obtained by summing % inhibition of FcεRI-induced degranulation by individual components of the complex mixtures (individual effects are provided in the rows labeled with names of the individual components).

FIG. 11 highlights predicted % inhibition of FcεRI-induced degranulation by a cannabinoid-containing complex mixture comprising cannabidiol and one of ENT 6, 8, or 9, (row labeled "predicted additive") and actual % inhibition by the complex mixtures (row labeled "actual"). The row labeled "Fold increase actual performance over predicted" shows ratios between predicted effects and actual effects.

Figure 12:
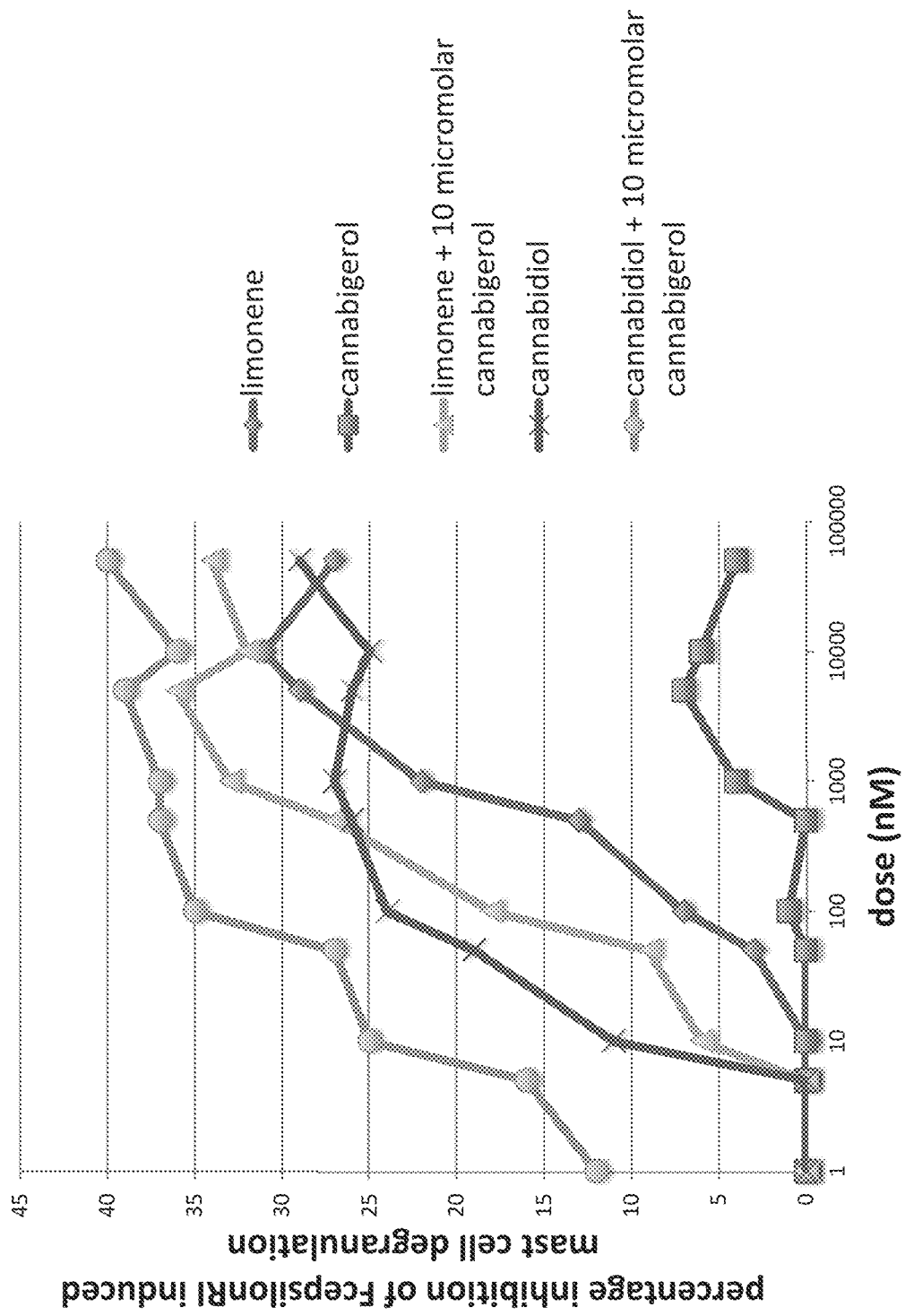

FIG. 12 presents % inhibition of FcεRI-induced degranulation by different concentrations of limonene (line with diamonds), different concentrations of cannabigerol (line with rectangles), different concentrations of limonene in combination with 10 μM cannabigerol (line with triangles), different concentrations of cannabidiol (line with x) and different concentrations of cannabidiol in combination with 10 μM cannabigerol (line with circles).

Figure 13:
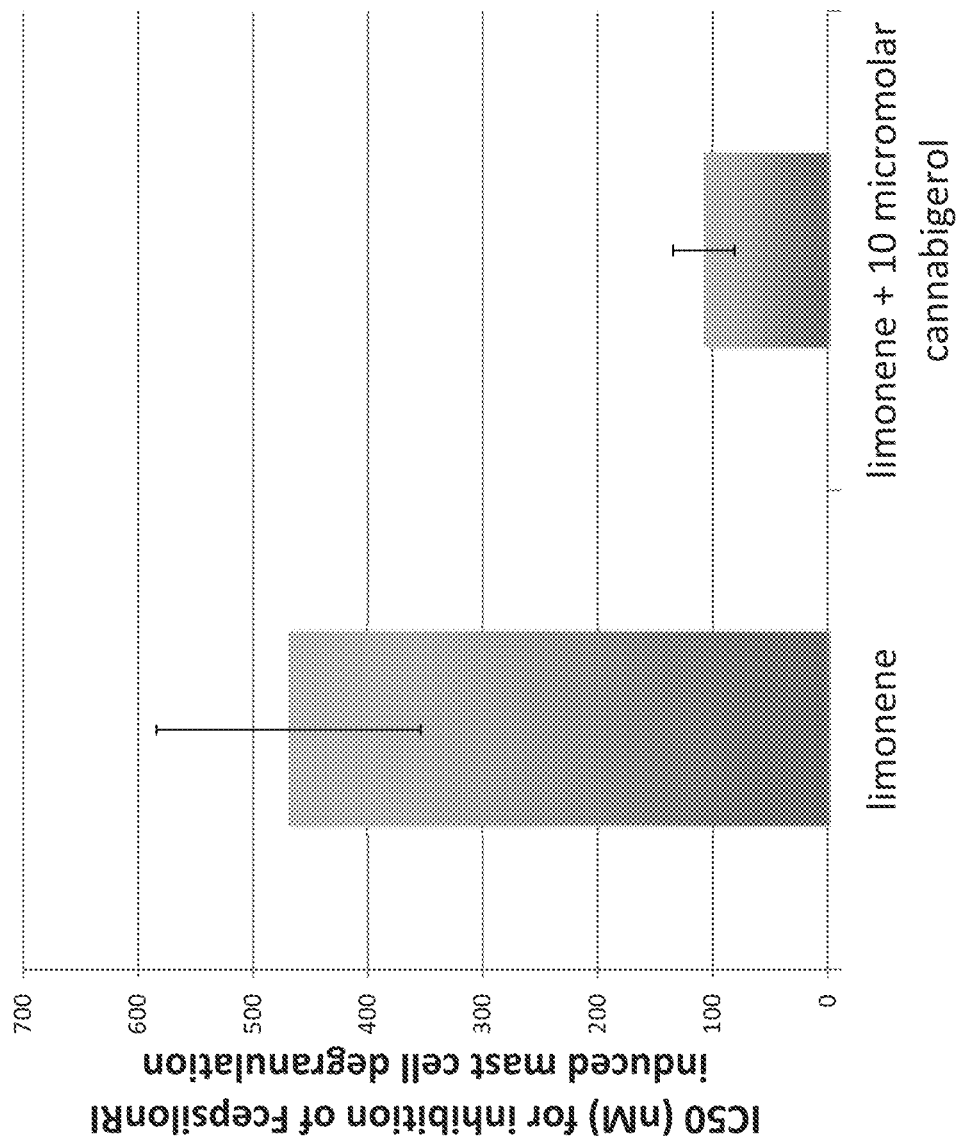

FIG. 13 compares potency of inhibition of FcεRI-induced degranulation by limonene alone (left) or by limonene in combination of 10 μM cannabigerol (right), calculated based on IC50 (nM) of % inhibition of FcεRI-induced degranulation presented in FIG. 12.

Figure 14:
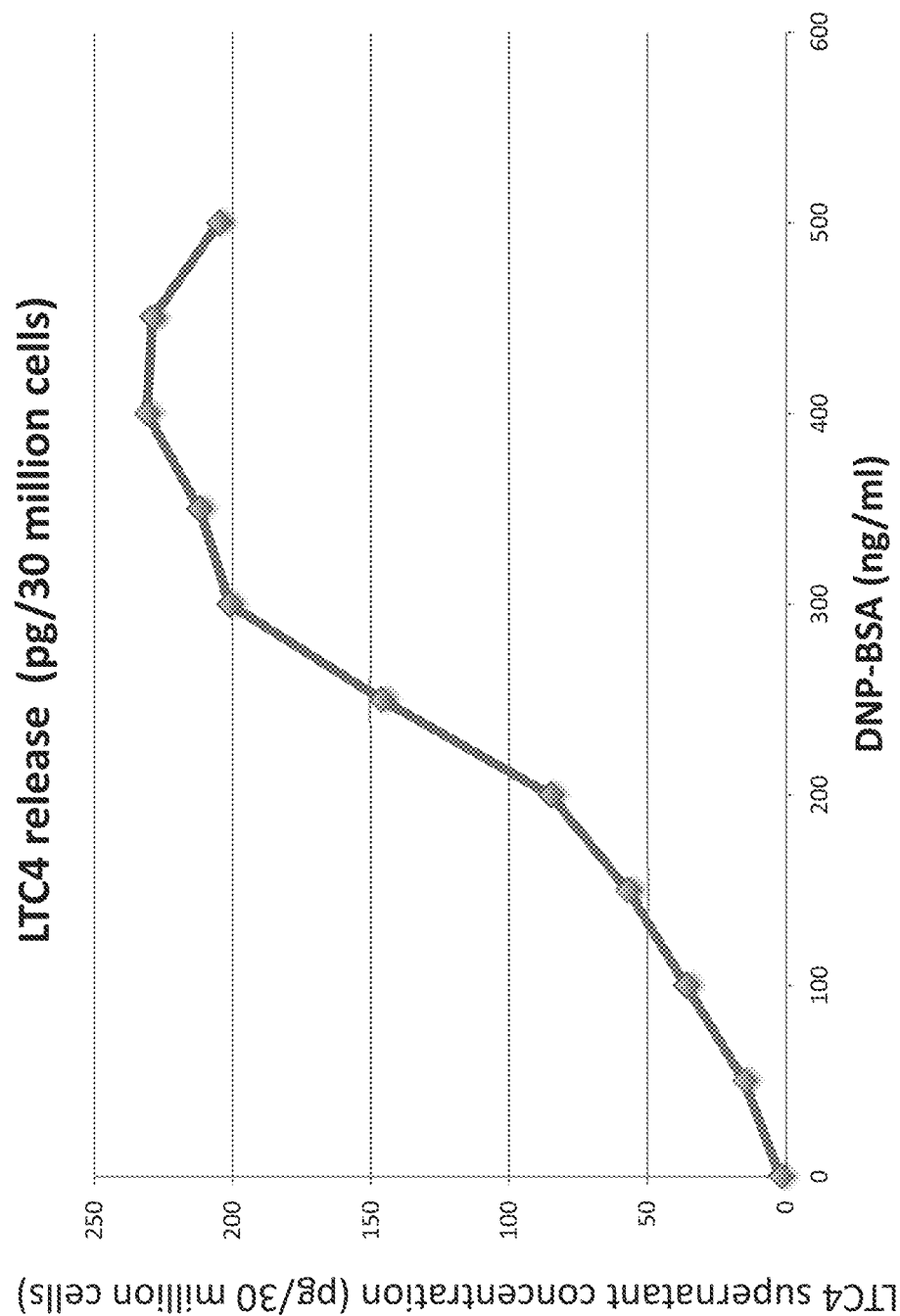

FIG. 14 shows amounts of leukotriene C4 (LTC4) release (y-axis, pg/30 million cells) in response to various concentrations of the FcεRI crosslinking agonist, DNP-BSA, ranging from 1 to 500 ng/ml.

FIG. 15 provides data from Example 5 illustrating FcεRI ligation-induced mast cell activation measured by the amount of LTC4 release, in the absence (Negative Control) or presence of various cannabinoid-containing complex mixtures comprising cannabidiol and one of five sub-mixtures (ENT 1A, 2, 3A, 8A and 9A). The table provides the amount of LTC4 release (pg/30 million cells), % release as compared to the control (i.e., LTC4 release in the absence of any cannabinoid-containing complex mixture), and % inhibition (% release subtracted from 100%).

Figure 16:
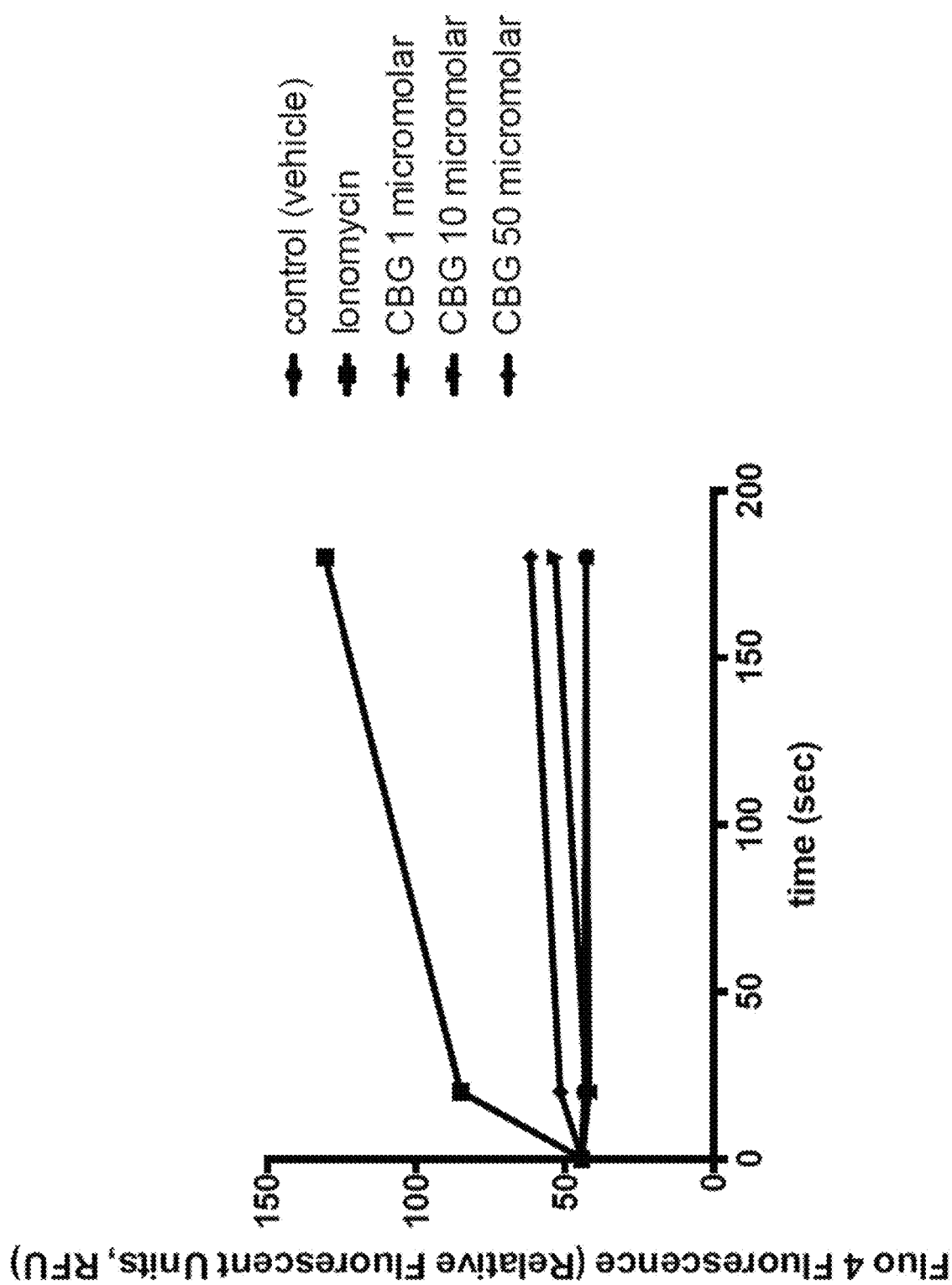

FIG. 16 provides data from Example 6 illustrating the intracellular free calcium measurements in the presence of external calcium (1 mM) in RBL2H3 cells stimulated in the absence (control vehicle) or presence of 1, 10, or 50 μM CBG. Ionomycin was used as a positive control. Stimuli were added at 20 s.

The figures depict various embodiments of the present invention for purposes of illustration only. One skilled in the art will readily recognize from the following discussion that alternative embodiments of the structures and methods illustrated herein may be employed without departing from the principles of the invention described herein.

5. DETAILED DESCRIPTION

5.1. Definitions

Unless defined otherwise, all technical and scientific terms used herein have the meaning commonly understood by a person skilled in the art to which this invention belongs. As used herein, the following terms have the meanings ascribed to them below.

"Major cannabinoid" means cannabidiol (CBD) or cannabinol (CBN). The major cannabinoid can be obtained by chemical synthesis, chemical modification, or obtained from plant materials derived from one or more *Cannabis* plants.

"Minor cannabinoid" means cannabichromene (CBC), cannabigerol (CBG), or cannabidivarin (CBV). The minor cannabinoid can be obtained by chemical synthesis, chemical modification, or obtained from plant materials derived from one or more *Cannabis* plants.

"Selected terpene" means limonene, linalool, nerolidol, pinene, or phytol. The selected terpene can be obtained by chemical synthesis, chemical modification, commercially available molecules, or obtained from plant materials derived from one or more *Cannabis* plants.

A "sub-mixture", or "ENT", is a mixture comprising a plurality of compounds selected from minor cannabinoids and/or selected terpenes as defined herein. Table 1 provides specific compositions of sub-mixtures, ENT 1-ENT12A tested in the Examples presented herein.

A "cannabinoid-containing complex mixture" is a composition comprising a major cannabinoid and a sub-mixture (ENT).

A pharmaceutically active ingredient (synonymously, active pharmaceutical ingredient or active ingredient) is "substantially free of THC" if the ingredient contains less than 0.3% (w/v) of delta-9 tetrahydrocannabinol. A pharmaceutical composition comprising a pharmaceutically active ingredient is "substantially free of THC" if the pharmaceutical composition contains less than 0.3% (w/v) of delta-9 tetrahydrocannabinol.

A "*Cannabis sativa* extract" is a composition obtained from *Cannabis sativa* plant materials by fluid and/or gas extraction, for example by supercritical fluid extraction (SFE) with $CO_2$. The *Cannabis sativa* extract typically contains major cannabinoids, minor cannabinoids, selected terpenes, and also other terpenes, phytocannabinoids, and secondary metabolites. For example, the *Cannabis sativa* extract can include one or more of bisabolol, humulene, terpinene, caryophyllene, camphene, geraniol, guaiol, isopulegoll, ocimene, cymene, eucalyptol, terpinolene, and myrcene.

5.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereo centers intends each stereoisomer, and all combinations of stereoisomers, thereof.

5.3. Overview of Experimental Results

As described more fully in the Example section, we generated various cannabinoid-containing complex mixtures and tested their ability to inhibit degranulation of mast cells.

Each of the complex mixtures was generated by combining the major cannabinoid, cannabidiol (CBD), with one of the twenty-one sub-mixtures identified in Table 1.

TABLE 1

| Sub-mixture | Components of sub-mixtures |
|---|---|
| ENT1 | 3 Minor Cannabinoids (Cannabichromene/Cannabigerol/Cannabidivarin) |
|  | 5 Selected Terpenes (Limonene/Linalool/Nerolidol/Pinene/Phytol) |
| ENT2 | 5 Selected Terpenes (Limonene/Linalool/Nerolidol/Pinene/Phytol) |
| ENT3 | 3 Minor Cannabinoids (Cannabichromene/Cannabigerol/Cannabidivarin) |
| ENT4 | 1 Minor Cannabinoid (Cannabichromene) |
|  | 5 Selected Terpenes (Limonene/Linalool/Nerolidol/Pinene/Phytol) |
| ENT5 | 1 Minor Cannabinoid (Cannabigerol) |
|  | 5 Selected Terpenes (Limonene/Linalool/Nerolidol/Pinene/Phytol) |
| ENT6 | 1 Minor Cannabinoid (Cannabidivarin) |
|  | 5 Selected Terpenes (Limonene/Linalool/Nerolidol/Pinene/Phytol) |
| ENT7 | 2 Minor Cannabinoids (Cannabichromene/Cannabigerol) |
| ENT8 | 2 Minor Cannabinoids (Cannabichromene/Cannabidivarin) |
| ENT9 | 2 Minor Cannabinoids (Cannabigerol/Cannabidivarin) |
|  | 5 Selected Terpenes (Limonene/Linalool/Nerolidol/Pinene/Phytol) |
| ENT10 | 3 Minor Cannabinoids (Cannabichromene/Cannabigerol/Cannabidivarin) |
|  | 2 Selected Terpenes (Limonene/Linalool) |
| ENT11 | 3 Minor Cannabinoids (Cannabichromene/Cannabigerol/Cannabidivarin) |
|  | 1 Selected Terpene (Nerolidol) |
| ENT12 | 3 Minor Cannabinoids (Cannabichromene/Cannabigerol/Cannabidivarin) |
|  | 2 Selected Terpenes (Pinene/Phytol) |
| ENT1A | 2 Minor Cannabinoids (Cannabichromene/Cannabigerol) |
|  | 5 Selected Terpenes (Limonene/Linalool/Nerolidol/Pinene/Phytol) |
| ENT3A | 2 Minor Cannabinoids (Cannabichromene/Cannabigerol) |
| ENT6A | 5 Selected Terpenes (Limonene/Linalool/Nerolidol/Pinene/Phytol) |
| ENT7A | 2 Minor Cannabinoids (Cannabichromene/Cannabigerol) |
| ENT8A | 1 Minor Cannabinoids (Cannabichromene) |
| ENT9A | 1 Minor Cannabinoids (Cannabigerol) |
|  | 5 Selected Terpenes (Limonene/Linalool/Nerolidol/Pinene/Phytol) |
| ENT10A | 2 Minor Cannabinoids (Cannabichromene/Cannabigerol) |
|  | 2 Selected Terpenes (Limonene/Linalool) |
| ENT11A | 2 Minor Cannabinoids (Cannabichromene/Cannabigerol) |
|  | 1 Selected Terpene (Nerolidol) |
| ENT12A | 2 Minor Cannabinoids (Cannabichromene/Cannabigerol) |
|  | 2 Selected Terpenes (Pinene/Phytol) |

The ability of these complex mixtures to inhibit mast cell degranulation was tested using an in vitro assay that has been widely used to identify anti-inflammatory agents.

FcεRI is a high-affinity receptor for the Fc region of immunoglobulin E (IgE), an antibody isotype involved in allergic disorders and immunity to parasites. Ligation of FcεRI molecules on the surface of mast cells induces degranulation and the synthesis and release of inflammatory mediators, such as leukotriene (LTC4). In the assay, mast cells are activated by artificial ligation of FcεRI molecules on the cell surface; activation is determined based on the release of histamine, beta-hexoseaminidase, and LTC4, both in the absence and in the presence of potential inhibitors.

We found that several of the cannabinoid-containing complex mixtures have significant inhibitory effects on FcεRI-induced degranulation of mast cells.

Figure 3:
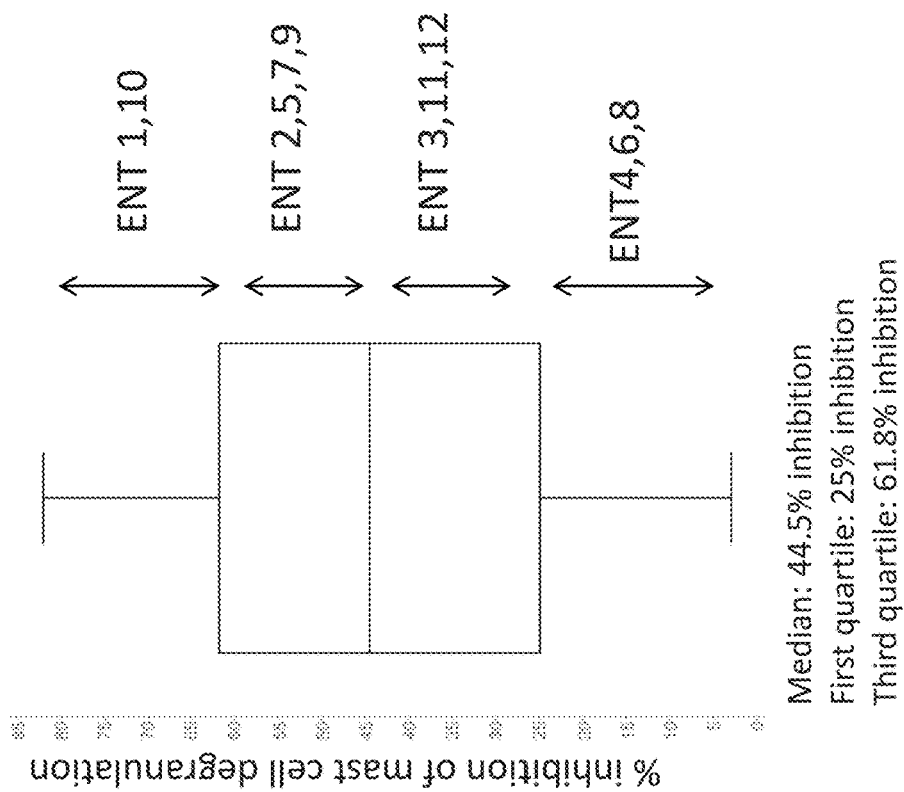

In particular, complex mixtures comprising cannabidiol and ENT 1, 5, 9 or 10 showed profound inhibitory effects (82%, 62%, 61%, and 63% inhibition, respectively) on mast cell degranulation measured by histamine release, as demonstrated in FIGS. 2 and 3. Many of the cannabinoid-containing complex mixtures—mixtures comprising ENT 1, 2, 3, 5, 7, 9 or 10—showed inhibitory effects significantly greater than the inhibitory effects of a nanomolar concentration of CP55940, a potent CB1 receptor agonist having effects similar to the effects of naturally-occurring delta-9 THC (shaded bar and horizontal line in FIG. 4). The results demonstrate that cannabinoid-containing complex mixtures that do not include THC can have strong anti-inflammatory effects, effects that exceed the effects of THC or CP55940, but without the psychoactive effects of THC.

The strong anti-inflammatory effects of cannabinoid-containing complex mixtures were greater than predicted from the separate anti-inflammatory effects observed using individual major cannabinoids, minor cannabinoids, or terpenes. As presented in FIG. 5, when used alone at 10 μM concentration, major and minor cannabinoids showed only modest effects on FcεRI-induced mast cell degranulation measured by histamine release. Specifically, cannabidiol (CBD), cannabinol (CBN), cannabichromene (CBC), and cannabigerol (CBG) suppressed FcεRI-induced degranulation about or less than 20%. Cannabidivarin (CBV) enhanced FcεRI-induced histamine secretion more than 20%. Thus, the predicted anti-inflammatory effects of a mixture comprising the three minor cannabinoids (ENT 3) and cannabidiol (CBD) is about 0, based on the sum of individual effects of three minor cannabinoids and cannabidiol (CBD); however, the actual inhibitory effect of the mixture comprising ENT 3 and cannabidiol was 43% (FIG. 6).

We further demonstrated that complex mixtures comprising ENT 1A showed profound inhibitory effects (73%) on de novo biosynthesis of bioactive lipid mediators by mast cells measured by LTC4 release, as demonstrated in FIG. 15. The cannabinoid-containing complex mixtures also had similar synergistic effects on LTC4 release. The predicted inhibitory effects of a complex mixture comprising cannabidiol (CBD), two minor cannabinoids and five selected terpenes (ENT1A) on LTC4 release were 57% when the individual inhibitory effects were summed (i.e., effects of a mixture with ENT2 and a mixture with ENT3A). However, the actual effect of the complex mixture was about 73%. Thus, the data suggest that certain cannabinoid-containing complex mixtures have synergistic effects, which were not expected from other experiments testing effects of each individual component or subsets of the complex mixtures.

The strong anti-inflammatory effects of cannabinoid-containing complex mixtures comprising cannabidivarin (CBV) were quite surprising in view of strong pro-inflammatory effects of cannabidivarin (CBV). Pro-inflammatory effects of cannabidivarin (CBV) used as single agent were further demonstrated in a time-course experiment provided in FIG. 7A. As illustrated in FIGS. 7A-7B, pretreatment of mast cells with 10 μM of cannabidivarin (CBV) for 10 minutes significantly enhanced pro-inflammatory effects of FcεRI ligation. Without wishing to be bound by any theory, the additive interaction between cannabidivarin (CBV) and FcεRI ligation suggests that cannabidivarin (CBV) and FcεRI act in independent pathways.

The synergistic effects were also demonstrated with cannabinoid-containing complex mixtures comprising terpenes. As shown in FIG. 8, each terpene, when tested individually, suppressed FcεRI-induced degranulation only about or far less than 20%. Thus, the predicted anti-inflammatory effects of a complex mixture comprising five terpenes and cannabidiol (CBD) was about 20% when the anti-inflammatory effects of individual components were summed. However, actual anti-inflammatory effects of the complex mixture comprising the five terpenes (ENT2) and cannabidiol (CBD) was larger than 50% (FIG. 9).

As further illustrated in FIG. 10, the synergistic effects were found in many, but not all, cannabinoid-containing complex mixtures. The row labeled "Predicted additive" provides predicted anti-inflammatory effects (i.e., a sum of anti-inflammatory effects of individual components), and the row labeled "Actual" provides the actual anti-inflammatory effect of various cannabinoid-containing complex mixtures.

We further discovered that cannabigerol (CBG) in particular provides strong synergistic effects. As demonstrated in FIG. 11, a cannabinoid-containing complex mixture comprising cannabigerol (CBG) found within a mixture comprising cannabidiol (CBD) and ENT 9 has much higher anti-inflammatory effects compared to similar cannabinoid-containing complex mixtures without cannabigerol (e.g., a mixture comprising cannabidiol (CBD) and ENT 6 or 8). For example, the only difference between ENT 6 and ENT 9 is the presence or absence of cannabigerol (CBG). However, differences in anti-inhibitory effects between the two complex mixtures, comprising either ENT 6 or 9, were quite significant. A complex mixture with ENT 6 suppressed FcεRI-induced degranulation by 3% while a complex mixture with ENT 9 suppressed 61%.

FIG. 12 presents % inhibition of FcεRI-induced degranulation by limonene, cannabigerol (CBG), or cannabidiol (CBD) at different concentrations ranging from 1 nM to 50 μM, and compares the effects with the effects induced by limonene or cannabidiol (CBD) in the presence of 10 μM cannabigerol (CBG). The data shows that cannabigerol (CBG) left shifts the dose-response curves of cannabidiol (CBD) and limonene, thus demonstrating that cannabigerol (CBG) enhances anti-inflammatory effects of cannabidiol (CBD) and limonene. Specifically, as shown in FIG. 13, the IC50 of inhibitory effects of limonene alone on FcεRI-induced degranulation was about 480 nM (left bar), but the IC50 of inhibitory effects of limonene in combination with 10 μM cannabigerol (CBG) was about 100 nM (right bar).

From these experiments, we have demonstrated certain novel cannabinoid-containing complex mixtures exert strong inhibitory effects on mast cell degranulation and de novo synthesis of bioactive lipid mediator such as LTC4. The cannabinoid-containing complex mixtures are free of delta-9 THC but are shown to have anti-inflammatory effects that exceed the effects of delta-9 THC or the THC mimetic, CP55940. These data predict efficacy of these cannabinoid-containing complex mixtures in preventing mast-cell associated inflammatory responses, and thus in treating symptoms of mast cell-associated inflammatory disorders, without inducing unwanted psychoactive effects of delta-9 THC.

5.4. Pharmaceutically Active Ingredient

5.4.1. Major Cannabinoid, Minor Cannabinoid, Selected Terpene

Accordingly, in a first aspect, pharmaceutically active ingredients (also referred to herein synonymously as "active ingredient" and "active pharmaceutical ingredient") are provided that comprise the major cannabinoid, cannabidiol (CBD); at least a first minor cannabinoid; at least a first selected terpene; and optionally, at least a second minor cannabinoid. In some embodiments, the first minor cannabinoid is cannabigerol (CBG).

In some embodiments, the active ingredient comprises a second minor cannabinoid. In some embodiments, the second minor cannabinoid is cannabichromene (CBC). In some embodiments, the second minor cannabinoid is cannabidivarin (CBV).

In some embodiments, the active ingredient further comprises a third minor cannabinoid. In some embodiments, the second and the third minor cannabinoids are cannabichromene (CBC) and cannabidivarin (CBV).

In some embodiments, the first selected terpene is limonene. In some embodiments, the first selected terpene is linalool.

In some embodiments, the active ingredient further comprises a second selected terpene. In some embodiments, the second selected terpene is limonene. In some embodiments, the second selected terpene is linalool. In some embodiments, the first and the second selected terpene are limonene and linalool, respectively.

In some embodiments, the active ingredient comprises limonene, linalool, pinene, and phytol.

5.4.1.1. Relative Content

In typical embodiments, cannabidiol (CBD) constitutes 7-25 percent by weight (wt %) of the active ingredient.

In certain embodiments, cannabidiol (CBD) constitutes 7-10 wt % of the active ingredient, 10-15 wt % of the active ingredient, 15-20 wt % of the active ingredient, 15-25 wt % of the active ingredient, or 20-25 wt % of the active ingredient. In certain embodiments, the major cannabinoids collectively constitute at least 5 wt %, at least 10 wt %, at least 15 wt %, or at least 20 wt %, but each case no more than 25 wt %, of the active ingredient.

In typical embodiments, the minor cannabinoids collectively constitute 15-65% by weight of the active ingredient.

In certain embodiments, the minor cannabinoids collectively constitute 15-20 wt % of the active ingredient, 20-25 wt % of the active ingredient, 25-30 wt % of the active ingredient, 30-35 wt % of the active ingredient, 35-40 wt % of the active ingredient. In certain embodiments, the minor cannabinoids collectively constitute 40-45 wt %, 45-50 wt %, 50-55 wt %, 55-60 wt %, or 60-65 wt % of the active ingredient. In certain embodiments, the minor cannabinoids collectively constitute at least 15 wt %, 20 wt %, 25 wt %, 30 wt %, 35 wt %, 40 wt %, 45 wt %, 50 wt %, 55 wt %, 60 wt %, but in each case no more than 65 wt %, of the active ingredient.

In typical embodiments, the selected terpenes collectively constitute 13-65% by weight of the active ingredient.

In certain embodiments, the selected terpenes collectively constitute at least 13 wt %, at least 15 wt %, at least 20 wt %, at least 25 wt %, at least 30 wt %, at least 35 wt %, at least 40 wt %, at least 45 wt %, at least 50 wt %, at least 55 wt %, or at least 60 wt %, but in each case less than 65 wt % of the active ingredient. In certain embodiments, the selected terpenes collectively constitute 13-65 wt % of the active ingredient, 18-65 wt % of the active ingredient, 18-25 wt % of the active ingredient, 25-55 wt % of the active ingredient, 30-50 wt % of the active ingredient, 25-30 wt % of the active ingredient, 30-35 wt % of the active ingredient, 35-40 wt % of the active ingredient, 40-45 wt % of the active ingredient, 45-50 wt % of the active ingredient, 50-55 wt % of the active ingredient, 55-60 wt % of the active ingredient, 60-65 wt % of the active ingredient.

In typical embodiments, cannabidiol (CBD) constitutes 7-25% (w/v) of the active ingredient.

In certain embodiments, cannabidiol (CBD) constitutes 7-10% (w/v) of the active ingredient, 10-15% (w/v) of the active ingredient, 15-20% (w/v) of the active ingredient, 15-25% (w/v) of the active ingredient, or 20-25% (w/v) of the active ingredient. In certain embodiments, the major cannabinoids collectively constitute at least 5% (w/v), at least 10% (w/v), at least 15% (w/v), or at least 20% (w/v), but each case no more than 25% (w/v), of the active ingredient.

In typical embodiments, the minor cannabinoids collectively constitute 15-65% (w/v) of the active ingredient.

In certain embodiments, the minor cannabinoids collectively constitute 15-20% (w/v) of the active ingredient, 20-25% (w/v) of the active ingredient, 25-30% (w/v) of the active ingredient, 30-35% (w/v) of the active ingredient, 35-40% (w/v) of the active ingredient. In certain embodiments, the minor cannabinoids collectively constitute 40-45% (w/v), 45-50% (w/v), 50-55% (w/v), 55-60% (w/v), or 60-65% (w/v) of the active ingredient. In certain embodiments, the minor cannabinoids collectively constitute at least 15% (w/v), 20% (w/v), 25% (w/v), 30% (w/v), 35% (w/v), 40% (w/v), 45% (w/v), 50% (w/v), 55% (w/v), 60% (w/v), but in each case no more than 65% (w/v), of the active ingredient.

In typical embodiments, the selected terpenes collectively constitute 13-65% (w/v) of the active ingredient.

In certain embodiments, the selected terpenes collectively constitute at least 13% (w/v), at least 15% (w/v), at least 20% (w/v), at least 25% (w/v), at least 30% (w/v), at least 35% (w/v), at least 40% (w/v), at least 45% (w/v), at least 50% (w/v), at least 55% (w/v), or at least 60% (w/v), but in each case less than 65% (w/v) of the active ingredient. In certain embodiments, the selected terpenes collectively constitute 13-65% (w/v) of the active ingredient, 18-65% (w/v) of the active ingredient, 18-25% (w/v) of the active ingredient, 25-55% (w/v) of the active ingredient, 30-50% (w/v) of the active ingredient, 25-30% (w/v) of the active ingredient, 30-35% (w/v) of the active ingredient, 35-40% (w/v) of the active ingredient, 40-45% (w/v) of the active ingredient, 45-50% (w/v) of the active ingredient, 50-55% (w/v) of the active ingredient, 55-60% (w/v) of the active ingredient, 60-65% (w/v) of the active ingredient.

In some currently preferred embodiments, cannabidiol (CBD) constitutes 7-25% (w/v) of the active ingredient; the minor cannabinoids collectively constitute 15-65% (w/v) of the active ingredient; and the selected terpenes collectively constitute 13-65% (w/v) of the active ingredient.

5.4.1.2. Absolute Content

In some embodiments, the pharmaceutically active ingredient consists of cannabidiol (CBD), minor cannabinoids, and selected terpenes. In these embodiments, cannabidiol (CBD), minor cannabinoids, and selected terpenes collectively constitute 100 wt % of the pharmaceutically active ingredient.

In some embodiments, the active ingredient consists essentially of cannabidiol (CBD), minor cannabinoids, and selected terpenes.

In other embodiments, cannabidiol (CBD), minor cannabinoids, and selected terpenes collectively constitute less than 100% by weight (wt %) of the pharmaceutically active ingredient.

In some embodiments, the pharmaceutically active ingredient consists of cannabidiol (CBD), minor cannabinoids, and selected terpenes. In these embodiments, cannabidiol (CBD), minor cannabinoids, and selected terpenes collectively constitute 100% (w/v) of the pharmaceutically active ingredient.

In some embodiments, the active ingredient consists essentially of cannabidiol (CBD), minor cannabinoids, and selected terpenes.

In other embodiments, the cannabidiol (CBD), minor cannabinoids, and selected terpenes collectively constitute less than 100% (w/v) of the pharmaceutically active ingredient.

5.4.2. Other Components

In some embodiments, the major cannabinoids, minor cannabinoids, and selected terpenes collectively constitute less than 100% by weight (wt %) of the pharmaceutically active ingredient.

In various such embodiments, the cannabidiol (CBD), minor cannabinoids, and selected terpenes collectively constitute at least 75% by weight, but less than 100 wt %, of the pharmaceutically active ingredient. In specific embodiments, the cannabidiol (CBD), minor cannabinoids, and selected terpenes collectively constitute at least 80%, at least at least 85%, at least 90%, at least 91%, at least 92%, at least 93%, at least 94%, or at least 95% by weight, but less than 100 wt %, of the active ingredient. In particular embodiments, cannabidiol (CBD), minor cannabinoids, and selected terpenes collectively constitute at least 96%, at least 97%, at least 98%, or at least 99% by weight, but less than 100 wt %, of the active ingredient.

In embodiments in which the cannabidiol (CBD), minor cannabinoids, and selected terpenes collectively constitute less than 100% by weight (wt %) of the pharmaceutically active ingredient, the active ingredient further comprises compounds other than the major cannabinoids, minor cannabinoids, and selected terpenes. In typical such embodiments, all other compounds in the active ingredient are extractable from *Cannabis sativa*. In specific embodiments, all other compounds in the active ingredient are present in an extract made from *Cannabis sativa*.

In some embodiments, the cannabidiol (CBD), minor cannabinoids, and selected terpenes collectively constitute less than 100% (w/v) of the pharmaceutically active ingredient.

In various such embodiments, the cannabidiol (CBD), minor cannabinoids, and selected terpenes collectively constitute at least 75% (w/v), but less than 100% (w/v), of the pharmaceutically active ingredient. In specific embodiments, the major cannabinoids, minor cannabinoids, and optional selected terpenes collectively constitute at least 80%, at least at least 85%, at least 90%, at least 91%, at least 92%, at least 93%, at least 94%, or at least 95% (w/v), but less than 100% (w/v), of the active ingredient. In particular embodiments, the major cannabinoids, minor cannabinoids, and optional selected terpenes collectively constitute at least 96%, at least 97%, at least 98%, or at least 99% (w/v), but less than 100% (w/v), of the active ingredient.

In embodiments in which the cannabidiol, minor cannabinoids, and selected terpenes collectively constitute less than 100% (w/v) of the pharmaceutically active ingredient, the active ingredient further comprises compounds other than the cannabidiol, minor cannabinoids, and selected terpenes. In typical such embodiments, all other compounds in the active ingredient are extractable from *Cannabis sativa*. In specific embodiments, all other compounds in the active ingredient are present in an extract made from *Cannabis sativa*.

5.4.2.1. Delta-9 Tetrahydrocannabinol (THC) Content

In various embodiments, the active ingredient is substantially free of delta-9 tetrahydrocannabinol (THC). These embodiments retain the therapeutic properties of the active pharmaceutical ingredient in treating immune disorders, and lack psychoactive effects, which offers certain regulatory and other physiological advantages.

In certain embodiments, the active ingredient is not substantially free of delta-9 THC. In certain of these embodiments, the active ingredient comprises 1-10 percent by weight (wt %) THC. In specific embodiments, the active ingredient comprises 2-9 wt % THC, 3-8 wt % THC, 4-7 wt % THC. In certain embodiments, the active ingredient comprises 1, 2, 3, 4, 5, 6, 7, 8, 9 or 10 wt % THC.

In certain embodiments, the active ingredient is not substantially free of delta-9 THC. In certain of these embodiments, the active ingredient comprises 1-10 percent (w/v) THC. In specific embodiments, the active ingredient comprises 2-9% (w/v) THC, 3-8% (w/v) THC, 4-7% (w/v) THC. In certain embodiments, the active ingredient comprises 1, 2, 3, 4, 5, 6, 7, 8, 9 or 10% (w/v) THC.

5.4.3. Process for Preparing Active Ingredient

In some embodiments, the pharmaceutically active ingredient is prepared by mixing chemically pure cannabidiol (CBD), minor cannabinoids, and selected terpenes to desired final concentrations. Each of the cannabidiol (CBD), minor cannabinoids, and selected terpenes can independently be chemically synthesized, either by total synthesis or by synthetic modification of an intermediate, purified from a compositional mixture such as a *Cannabis sativa* extract, or, as in the Examples described below, purchased commercially.

In other embodiments, the pharmaceutically active ingredient is prepared from a starting compositional mixture by adjusting to predetermined desired final concentrations any one or more of cannabidiol (CBD), minor cannabinoids, and selected terpenes. In typical embodiments, the starting compositional mixture is a *Cannabis sativa* extract. In currently preferred embodiments, the starting compositional mixture is a *Cannabis sativa* extract and one or more of the cannabidiol (CBD), minor cannabinoids, and optional selected terpenes is added to the mixture to achieve predetermined desired final concentrations.

Typically in such embodiments, the process further comprises the earlier step of determining the concentration of each desired cannabidiol (CBD), minor cannabinoid, and optional selected terpene in the starting compositional mixture.

In certain of these embodiments, the process further comprises the still earlier step of preparing a *Cannabis sativa* extract. Methods of preparing *Cannabis sativa* extracts are described in U.S. Pat. Nos. 6,403,126, 8,895,078, and 9,066,910; Doorenbos et al., Cultivation, extraction, and analysis of *Cannabis sativa* L., Annals of The New York Academy of Sciences, 191, 3-14 (1971); Fairbairn and Liebmann, The extraction and estimation of the cannabinoids in *Cannabis sativa* L. and its products, Journal of Pharmacy and Pharmacology, 25, 150-155 (1973); Oroszlan and Verzar-petri, Separation, quantitation and isolation of cannabinoids from *Cannabis sativa* L. by overpressured layer chromatography, Journal of Chromatography A, 388, 217-224 (1987), the disclosures of which are incorporated herein by reference in their entireties. In particular embodiments, the extraction method is chosen to provide an extract that has a content of cannabidiol, minor cannabinoids, and selected terpenes that best approximates the predetermined composition of the active ingredient.

In some embodiments, the process further comprises a first step of selecting a *Cannabis sativa* strain for subsequent development as a therapeutic agent or a source of extracted compounds for therapy.

In certain embodiments, the strain selected has a typical content in the plant as a whole, or in an extractable portion thereof, of cannabidiol, minor cannabinoids, and selected terpenes that best approximates the predetermined composition of the active ingredient. In specific embodiments, the strain selected has a typical content in the plant, extractable portion thereof, or extract thereof, that best approximates the predetermined weight ratios of desired major cannabinoids, minor cannabinoids, and optional selected terpenes. In specific embodiments, the strain selected has a typical content in the plant, extractable portion thereof, or extract thereof, that requires adjustment in concentration of the fewest number of the desired cannabidiol (CBD), minor cannabinoids, and selected terpenes to achieve the predetermined composition of the active ingredient. In specific embodiments, the strain selected has a typical content in the plant, extractable portion thereof, or extract thereof, that requires the least expensive adjustment in concentration of the desired cannabidiol (CBD), minor cannabinoids, and optional selected terpenes to achieve the predetermined composition of the active ingredient.

Cannabinoid, terpenoid, and other chemical contents can be measured via any appropriate analytical chemistry method known in the art. The methods include, but not limited to, Gas Chromatography (GC) coupled with secondary detection methods such as Mass Spectroscopy (GC-MS), tandem MS (GC-MS/MS), Flame Ionization Detector (GC-FID), or Infrared Spectroscopy (GC-IR). Liquid Chromatography (LC) can be coupled with the secondary detection methods.

5.4.4. Product by Process

In typical embodiments, the pharmaceutically active ingredient is prepared by one of the processes described in Section 5.4.3 above.

In embodiments in which the pharmaceutically active ingredient is prepared from a starting compositional mixture by adjusting to predetermined desired final concentrations any one or more of the cannabidiol (CBD), minor cannabinoids, and selected terpenes, all compounds in the active ingredient other than cannabidiol (CBD), minor cannabinoids, and selected terpenes are present within the starting compositional mixture. In embodiments in which the starting compositional mixture is a *Cannabis sativa* extract, all compounds in the active ingredient other than cannabidiol (CBD), minor cannabinoids, and optional selected terpenes are present within the *Cannabis sativa* extract.

5.5. Pharmaceutical Compositions

In another aspect, pharmaceutical compositions are provided. The pharmaceutical composition comprises the pharmaceutically active ingredient disclosed herein and a pharmaceutically acceptable carrier or diluent.

5.5.1. Content of pharmaceutically active ingredient

In typical embodiments, the active ingredient is present in the pharmaceutical composition at a concentration of at least 0.01 µg/ml, at least 0.1 µg/ml, at least 0.5 µg/ml, or at least 1 µg/ml. In certain embodiments, the active ingredient is present in the pharmaceutical composition at a concentration of at least 1 µg/ml, 2 µg/ml, 3 µg/ml, 4 µg/ml, 5 µg/ml, 10 µg/ml, 15 µg/ml, 20 µg/ml, or 25 µg/ml. In certain embodiments, the active ingredient is present in the pharmaceutical composition at a concentration of at least 30 µg/ml, 35 µg/ml, 40 µg/ml, 45 µg/ml or 50 µg/ml.

5.5.2. Formulation Generally

The pharmaceutical composition can be in any form appropriate for human or veterinary medicine, including a liquid, an oil, an emulsion, a gel, a colloid, an aerosol or a solid.

The pharmaceutical composition can be formulated for administration by any route of administration appropriate for human or veterinary medicine, including enteral and parenteral routes of administration.

In various embodiments, the pharmaceutical composition is formulated for administration by inhalation. In certain of these embodiments, the pharmaceutical composition is formulated for administration by a vaporizer. In certain of these embodiments, the pharmaceutical composition is formulated for administration by a nebulizer. In certain of these embodiments, the pharmaceutical composition is formulated for administration by an aerosolizer.

In various embodiments, the pharmaceutical composition is formulated for oral administration, for buccal administration, or for sublingual administration.

In some embodiments, the pharmaceutical composition is formulated for intravenous, intramuscular, or subcutaneous administration.

In some embodiments, the pharmaceutical composition is formulated for intrathecal or intracerebroventricular administration.

In some embodiments, the pharmaceutical composition is formulated for topical administration.

5.5.3. Pharmacological Compositions Adapted for Administration by Inhalation In some embodiments, unit dosage forms of the pharmaceutical composition described herein are provided, which are adapted for administration of the pharmaceutical composition by vaporizer, nebulizer, or aerosolizer. In some embodiments, the dosage form is a vial, an ampule, optionally scored to allow user opening. In particular embodiments, the nebulizer is a jet nebulizer or an ultrasonic nebulizer.

Inhalable compositions are generally administered in an aqueous solution e.g., as a nasal or pulmonary spray. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; M. Naef et al. Development and pharmacokinetic characterization of pulmonal and intravenous delta-9-tetrahydrocannabinol (THC) in humans, J. Pharm. Sci. 93, 1176-84 (2004); and in U.S. Pat. Nos. 4,778,810; 6,080,762; 7,052,678; and 8,277,781 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Mucosal formulations are administered as dry powder formulations e.g., comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 micron MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

5.5.4. Pharmacological Compositions Adapted for Oral/Buccal/Sublingual Administration Formulations for oral, buccal or sublingual administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral, buccal or sublingual administration (capsules, tablets, pills, dragees, powders, granules, and the like), one or more therapeutic agents may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

5.5.5. Pharmacological Compositions Adapted for Injection

For intravenous, intramuscular, or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In various embodiments, the unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the cannabinoid composition. In some embodiments, the unit dosage form contains 125 mg, 150 mg, 175 mg, or 200 mg of the cannabinoid composition. In some embodiments, the unit dosage form contains 250 mg of the cannabinoid composition.

In typical embodiments, the pharmaceutical composition in the unit dosage form is in liquid form. In various embodiments, the unit dosage form contains between 0.1 mL and 50 ml of the pharmaceutical composition. In some embodiments, the unit dosage form contains 1 ml, 2.5 ml, 5 ml, 7.5 ml, 10 ml, 25 ml, or 50 ml of pharmaceutical composition.

In particular embodiments, the unit dosage form is a vial containing 1 ml of the cannabinoid composition at a concentration of 0.01 mg/ml, 0.1 mg/ml, 0.5 mg/ml, or 1 mg/ml. In some embodiments, the unit dosage form is a vial containing 2 ml of the cannabinoid composition at a concentration of 0.01 mg/ml, 0.1 mg/ml, 0.5 mg/ml, or 1 mg/ml.

In some embodiments, the pharmaceutical composition in the unit dosage form is in solid form, such as a lyophilate, suitable for solubilization.

Unit dosage form embodiments suitable for subcutaneous, intradermal, or intramuscular administration include preloaded syringes, auto-injectors, and autoinject pens, each containing a predetermined amount of the pharmaceutical composition described hereinabove.

In various embodiments, the unit dosage form is a preloaded syringe, comprising a syringe and a predetermined amount of the pharmaceutical composition. In certain preloaded syringe embodiments, the syringe is adapted for subcutaneous administration. In certain embodiments, the syringe is suitable for self-administration. In particular embodiments, the preloaded syringe is a single use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an autoinject pen. The autoinject pen comprises an autoinject pen containing a pharmaceutical composition as described herein. In some embodiments, the autoinject pen delivers a predetermined volume of pharmaceutical composition. In other embodiments, the autoinject pen is configured to deliver a volume of pharmaceutical composition set by the user.

In various embodiments, the autoinject pen contains about 0.1 mL to about 5.0 mL of the pharmaceutical composition. In specific embodiments, the autoinject pen contains about 0.5 mL of the pharmaceutical composition. In particular embodiments, the autoinject pen contains about 1.0 mL of the pharmaceutical composition. In other embodiments, the autoinject pen contains about 5.0 mL of the pharmaceutical composition.

5.5.6. Pharmacological Compositions Adapted for Topical Administration

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the cannabinoid-containing complex mixtures featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearoylphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). The cannabinoid-containing complex mixtures featured in the invention may be encapsulated within liposomes or may form complexes thereto, in particular to cationic liposomes. Alternatively, the cannabinoid-containing complex mixtures may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-10 alkyl ester (e.g., isopropylmyristate IPM), monoglyceride, diglyceride or pharmaceutically acceptable salt thereof.

5.6. Dose Ranges, Generally

In vivo and/or in vitro assays may optionally be employed to help identify optimal dosage ranges for use. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

5.7. Unit Dosage Forms

The pharmaceutical compositions may conveniently be presented in unit dosage form.

The unit dosage form will typically be adapted to one or more specific routes of administration of the pharmaceutical composition.

In various embodiments, the unit dosage form is adapted for administration by inhalation. In certain of these embodiments, the unit dosage form is adapted for administration by a vaporizer. In certain of these embodiments, the unit dosage form is adapted for administration by a nebulizer. In certain of these embodiments, the unit dosage form is adapted for administration by an aerosolizer.

In various embodiments, the unit dosage form is adapted for oral administration, for buccal administration, or for sublingual administration.

In some embodiments, the unit dosage form is adapted for intravenous, intramuscular, or subcutaneous administration.

In some embodiments, the unit dosage form is adapted for intrathecal or intracerebroventricular administration.

In some embodiments, the pharmaceutical composition is formulated for topical administration.

The amount of active ingredient which can be combined with a carrier material to produce a single dosage form will generally be that amount of the compound which produces a therapeutic effect.

5.8. Methods of Use

5.8.1. Methods of Treating Mast Cell-Associated or Basophil-Mediated Inflammatory Disorders In another aspect, methods are presented for treating a subject having a disease of the immune system. In typical embodiments, the disease of the immune system is a mast cell-associated inflammatory disorder. In some embodiments, the disease of the immune system is a basophil-mediated inflammatory disorder. In some embodiments, the immune system disease is a disease of the immune system in human subjects. In some embodiments, the immune system disease is a disease of the immune system in non-human animal subjects.

Diseases that can be treated with the cannabinoid-containing complex mixtures described herein include, but are not limited to: (1) allergy or atopy (e.g., allergic asthma, allergic rhinitis, eczema, allergic urticarial), (2) Mast Cell Activation Syndrome ("MCAS"), (3) physical and chemical urticarias, (4) idiopathic urticaria, (5) Crohn's Disease, (6) inflammatory bowel disease, (7) arthritis, including rheumatoid arthritis, (8) dermatitis or contact dermatitis, and (9) dermal, tissue or systemic responses to a sting, envenomation of other anaphylactic or anaphylactoid stimulus. The diseases further include canine mastocytosis, and allergy and inflammation in cattle, swine, etc.

Diseases that can be treated with the cannabinoid-containing complex mixtures described herein include, but are not limited to, diseases involving dysregulation of or diseases affected by one or more mast cell or basophil mediators, preformed mediators selected from the group consisting of histamine, mast cell or basophil proteases including, but not limited to, chymase and tryptase, serotonin, and heparin. In some embodiments, the mast cell or basophil mediators are newly synthesized mediators selected from the group consisting of bioactive lipids (including but not limited to prostaglandins and leukotrienes), PAF, cytokines, growth factors, chemokines, free radicals, and Substance P.

Diseases that can be treated with a cannabinoid-containing complex mixture as described herein further include, but are not limited to, diseases involving hyper-activation of mast cells by various activators, such as receptor-binding agonists (e.g., IgE+Antigen or IgE alone, IgG, Ig light chain, Complement, Neuropeptides, Microbial products, Cytokines, Chemokines), physical activators (e.g., mechanical perturbation, temperature, pressure), and small molecules (e.g., secretagogue peptide, arachidonic acid metabolites).

Diseases that can be treated with a cannabinoid-containing complex mixture further include, but are not limited to, diseases involving hyper-activation of basophils by various activators.

Diseases that can be treated with a cannabinoid-containing complex mixture described herein also include diseases related to abnormal degranulation of mast cells or basophils.

Diseases that can be treated with a cannabinoid-containing complex mixture described herein also include diseases related to abnormal synthesis of bioactive lipid mediators. In typical embodiments, the cannabinoid-containing complex mixtures are administered in the form of a pharmaceutical composition as described above. These methods are particularly aimed at therapeutic and prophylactic treatments of mammals, and more particularly, humans.

The terms "treatment," "treating," and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method includes subjects suffering from the undesirable condition or disease, as well as subjects at risk for development of the condition or disease.

By the term "therapeutically effective dose" or "effective amount" is meant a dose or amount that produces the desired effect for which it is administered. The exact dose or amount will depend on the purpose of the treatment, and will be ascertainable by one skilled in the art using known techniques (see, e.g., Lloyd (2012) The Art, Science and Technology of Pharmaceutical Compounding, Fourth Edition).

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "ameliorating" refers to any therapeutically beneficial result in the treatment of a disease state, e.g., an immune disorder, including prophylaxis, lessening in the severity or progression, remission, or cure thereof.

The actual amount administered, and rate and time-course of administration, will depend on the nature and severity of disease being treated. Prescription of treatment, e.g. decisions on dosage etc., is within the responsibility of general practitioners and other medical professionals, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, the pharmaceutical composition is administered by inhalation, orally, by buccal administration, by sublingual administration, by injection or by topical application.

In some embodiments, the pharmaceutical composition is administered in an amount sufficient to modulate degranulation of mast cells or basophils.

In some embodiments, the pharmaceutical composition is administered in an amount sufficient to modulate histamine release from mast cells or basophils. In some embodiments, the pharmaceutical composition is administered in an amount sufficient to modulate release of other mediator from mast cells or basophils, such as preformed mediators (e.g., histamine, mast cells proteases including, but not limited to, chymase and tryptase, serotonin, and heparin), or release of newly synthesized mediators (e.g., bioactive lipids (including but not limited to prostaglandins and leukotrienes), PAF, cytokines, growth factors, chemokines, free radicals, and Substance P.

In some embodiments, cannabidiol is administered in an amount less than 1 g, less than 500 mg, less than 100 mg, less than 10 mg per dose.

In some embodiments, the pharmaceutical composition is administered once a day, 2-4 times a day, 2-4 times a week, once a week, or once every two weeks.

A composition can be administered alone or in combination with other treatments, either simultaneously or sequentially dependent upon the condition to be treated.

Current inventions provide novel compositions comprising cannabidiol and sub-mixtures. We have demonstrated that the compositions have significant anti-inflammatory effects and thereby, they can have therapeutic effects on immune disorders, which involve hyper-inflammatory responses such as abnormally increased histamine release from mast cells. Furthermore, we have identified specific combinations of major cannabinoid and sub-mixtures that exert significant synergistic effects. This invention further provides methods of treating immune disorders using the pharmacological compositions identified herein.

5.9. Examples

The following examples are provided by way of illustration not limitation.

5.9.1. Example 1

Sub-Mixtures Comprising Minor Cannabinoids and/or Terpenes (ENT 1-ENT 12A)

Twenty one different sub-mixtures (ENT 1-ENT 12A) comprising minor cannabinoids and/or terpenes were generating by mixing individual components as specified in Table 1. Individual components were obtained from various vendors—nerolidol from Tokyo Chemical Industry (#N0454), linalool from Tokyo Chemical Industry (#L0048), a-pinene from Sigma Aldrich (#P45680), limonene from MP Biomedicals (#155234), phytol from Ultr Scientific (#FLMS-035), cannabidivarin from Sigma Aldrich (#C-140), cannabichromene from Sigma Aldrich (#C-143), cannabidiol from Sigma Aldrich (#C-045), cannabigerol from Sigma Aldrich (#C-141) and cannabinol from Sigma Aldrich (#C-046). Each component was added in an amount to make each sub-mixture comprise the same molar concentration of each individual component.

Similarly, cannabinoid-containing complex mixtures were generated by mixing a major cannabinoid (e.g., cannabidiol) and each component of the twenty one different sub-mixtures (ENT 1-12A). Each component (cannabidiol and each component of the sub-mixtures) was added in an amount sufficient to make the cannabinoid-containing complex mixtures comprise the same molar concentration of each individual component.

5.9.2. Example 2

Anti-Inflammatory Effects of Cannabinoid-Containing Complex Mixtures Measured Based on Inhibition of Histamine Release Anti-inflammatory effects of various cannabinoid-containing complex mixtures comprising cannabidiol and one of the twelve sub-mixtures (ENT 1-12) were tested by an in vitro assay based on FcεRI ligation.

FcεRI is a high-affinity receptor for the Fc region of immunoglobulin E (IgE), an antibody isotype involved in the allergy disorder and parasites immunity. FcεRI is multimeric and is a member of a family of related antigen/Fc receptors which have conserved structural features and similar roles in initiating intracellular signaling cascades. In humans, FcεRI controls the activation of mast cells and basophils, and participates in IgE-mediated antigen presentation. Multivalent antigens bind and crosslink IgE molecules held at the cell surface by FcεRI.

Receptor aggregation induces multiple signaling pathways that control diverse effector responses. These include the secretion of allergic mediators and induction of cytokine gene transcription, resulting in secretion of molecules such as interleukin-4, interleukin-6, tumor-necrosis factor-alpha and granulocyte-macrophage colony-stimulating factor. FcεRI is therefore central to the induction and maintenance of an allergic response and may confer physiological protection in parasitic infections. Thus, FcεRI has been commonly used in assays for identifying anti-inflammatory agents.

For the FcεRI assay, mast cells (from a mast cell line, RBL2H3) were plated in cluster plates at $5 \times 10^4$ cells/well. Monolayers were washed and incubated in 200 μl Tyrode's buffer. The mast cells were then primed with 1 μg/ml IgE-anti-DNP antibodies for 16 hours. The cells were then washed three times and a cannabinoid-containing complex mixture, prepared as above-described, was applied. The tested complex mixtures were applied in an amount calculated to expose the mast cells to 10 μM of cannabidiol and 10 μM of each minor cannabinoid or terpene component. Control for maximal FcεRI ligation-induced degranulation included no cannabinoid-containing complex mixture.

After 10 minutes, 250 ng/ml of DNP-BSA was applied to ligate FcεRI molecules on the mast cell surface.

Mast cell culture medium was collected 60 minutes after exposure to DNP-BSA with or without a tested cannabinoid-containing complex mixture. Degranulation of the mast cells was tested by measuring histamine release using a commercial ELISA kit (e.g., histamine ELISA kit available from ENZO Life Sciences, Inc., Rocky Mountain Diagnostics, Inc., etc.).

FIG. 2 shows mast cell degranulation after exposure to a cannabinoid-containing complex mixture comprising cannabidiol (CBD) and one of the twelve sub-mixtures (ENT 1-12). Mast cell degranulation for each tested complex mixture was measured based on the amount of histamine release and is presented as % histamine release compared to histamine release in response to PMA/Ionomycin (100%). Each complex mixture was tested in twenty-four (8×3) independent experiments and data from the twenty four independent experiments were averaged. The averaged values are presented as a bar for each complex mixture in FIG. 2. Standard deviations are also provided in the graph.

As shown in FIG. 2, certain cannabinoid-containing complex mixtures suppress mast degranulation quite significantly. Data for cannabinoid-containing complex mixtures having significant inhibitory effects on mast cell degranulation ($p<0.05$) are presented with solid bars and data with no significant effects are presented with shaded bars.

The % degranulation in response to each cannabinoid-containing complex mixture was used to calculate % inhibition of degranulation by subtracting the % degranulation from 100%. The % inhibition of degranulation by each cannabinoid-containing complex mixture is provided in the table of FIG. 3A (fourth row).

We then ranked the order of the tested complex mixtures based on their effects on mast cell degranulation (second and third row of FIG. 3A). As provided in FIG. 3A, a mixture comprising cannabidiol and ENT 1 was the most effective in suppressing mast cell degranulation, a mixture comprising cannabidiol and ENT 10 was the second, and a mixture comprising cannabidiol and ENT 5 was the third. A mixture comprising cannabidiol and ENT6 was the least effective. FIG. 3B further provides a box-raster plot of the data representing anti-inflammatory effects of various cannabinoid-containing complex mixtures. Arrows on the right side of the box-raster plot represents different quartiles in the distribution and complex mixtures corresponding to each quartile. Complex mixtures comprising ENT 1 or 10 were within third quartile with the most significant inhibitory effects, complex mixtures comprising ENT 2, 3, 5, 7, 9, 11, or 12 were within the median group with moderate inhibitory effects, and complex mixtures comprising ENT 4, 6, or 8 were within the first quartile with the least inhibitory effects.

Anti-inflammatory effects of CP55940, an agonist of CB1 receptor having effects similar to the effects of naturally-occurring THC, was also tested with a similar in vitro assay using FcεRI ligation to drive mast cell degranulation. As demonstrated in FIG. 4, CP55940 suppressed histamine release of mast cells about 30% compared to PMA/Iomomycin (100%). The effect is less than effects shown by a number of cannabinoid-containing complex mixtures provided herein. For example, complex mixtures comprising cannabidiol and ENT 1, 2, 3, 5, 7, 9, or 10 had stronger inhibitory effects than CP55940 (FIG. 4).

From this series of experiments, we have demonstrated that several cannabinoid-containing complex mixtures strongly suppress degranulation of mast cells, predicting efficacy of these complex mixtures as anti-inflammatory agents for treatment of diverse immune disorders. Moreover, their efficacy was observed in the absence of THC and their anti-inflammatory effects were greater than effects of CP55940 (FIG. 4). This suggests that cannabinoid-containing complex mixtures not comprising THC can be effective in preventing inflammatory responses, and thus in treating symptoms of inflammatory disorders.

5.9.3. Example 3

Anti-Inflammatory Effects of Each Major or Minor Cannabinoid, or Selected Terpene Anti-inflammatory effects of (i) each major cannabinoid, (ii) each minor cannabinoid, and (iii) each selected terpene, were assessed based on their inhibition of FcεRI-induced mast cell degranulation by measuring histamine release as described above.

FIG. 5 shows anti-inflammatory effects of each major cannabinoid (cannabidiol and cannabinol) and each minor cannabinoid (cannabichromene, cannabigerol and cannabidivarin) at 10 µM concentration. FIG. 8 shows anti-inflammatory effects of each selected terpene (limonene, linalool, nerolidol, pinene, and phytol) at 10 µM concentration. Their anti-inflammatory effects are presented as % reduction of histamine release in the presence of the tested compound compared to the histamine release in the presence of PMA/Ionomycin (0%). Standard deviations of the experimental data are also provided in the graphs.

Some major and minor cannabinoids and selected terpenes suppressed histamine release, demonstrating anti-inflammatory effects. For example, cannabidiol (CBD) and limonene reduced FcεRI ligation-induced histamine secretion by 23% and 24%, respectively. However, most of minor cannabinoids (e.g., cannabichromene, cannabigerol) and selected terpenes (e.g., linalool, nerolidol, pinene, phytol) showed almost no anti-inflammatory effects.

Furthermore, cannabidivarin showed pro-inflammatory effects. As shown in FIG. 5, cannabidivarin increased FcεRI ligation-induced histamine secretion by 26%. Pro-inflammatory effects of cannabidivarin were further demonstrated in a time-lapse experiment, data from which are provided in FIG. 7. FIG. 7A shows time-course of histamine release in response to FcεRI ligation with (dotted line) or without (solid line) pretreatment with 10 µM of cannabidivarin for 10 minutes. The x-axis represents minutes after application of BSA-DNP and y-axis represents the amount of histamine release (pg/10 million cells). Pro-inflammatory effects of cannabidivarin was even greater than effects of FcεRI ligation; histamine release in response to FcεRI ligation was about 220 pg/10 million cells after 10 minute exposure, while histamine release in response to cannabidivarin (without concurrent FcεRI ligation) was about 340 pg/10 million cells. Ligating FcεRI after pretreatment with cannabidivarin further enhanced pro-inflammatory effects, suggesting that cannabidivarin and FcεRI ligation act through independent pathways.

Accordingly, the profound anti-inflammatory effects of cannabinoid-containing complex mixtures identified herein could not have been expected from the anti-inflammatory effects of the individual major cannabinoid, individual minor cannabinoid and individual selected terpenes. In particular, the profound anti-inflammatory effects of cannabidivarin-containing complex mixtures identified herein could not have been expected from anti-inflammatory effects of cannabidivarin which, when used alone, triggers significant mast cell degranulation.

For example, when anti-inflammatory effects of cannabinoid-containing complex mixtures are predicted based on the sum of anti-inflammatory effects of their individual components, the predicted values are far less than the actual anti-inflammatory effects of cannabinoid-containing complex mixtures. For example, predicted inhibitory effects of a complex mixture comprising cannabidiol and three minor cannabinoid (ENT3) on mast cell degranulation were only about 1%, but the actual observed effect of the complex mixture was about 43% (FIGS. 6 and 10). Similarly, predicted inhibitory effects of a complex mixture comprising cannabidiol and five selected terpenes (ENT 2) on mast cell degranulation were about 23%, but their actual observed effects as a complex mixture were about 55% (FIGS. 9 and 10). FIG. 10 provides a full list of actual anti-inflammatory effects (in the row labeled "Actual") and predicted effects (in the row labeled "Predicted additive) for each of the tested cannabinoid-containing complex mixtures. The ratios between the actual effects and the predicted value are also provided in the row labeled "Fold increase actual performance over predicted additive" of FIG. 10. The list shows big discrepancies between predicted values and actual values for many cannabinoid-containing complex mixtures.

In particular, it would have been expected that complex mixtures comprising cannabidivarin would have no or minimal anti-inflammatory effects, given that cannabidivarin when used alone has profound pro-inflammatory effects. However, contrary to the expectation, several cannabinoid-containing complex mixtures comprising cannabidivarin—such as a mixture comprising cannabidiol and ENT 1, a mixture comprising cannabidiol and ENT 10 and a mixture comprising cannabidiol and ENT 9—had strong anti-inflammatory effects.

This demonstrates that unknown synergistic interactions between components play an important role in anti-inflammatory effects of many of the cannabinoid-containing complex mixtures. The synergistic effects were not expected from the studies performed on individual components of the complex mixtures.

5.9.4. Example 4

Synergistic Effects of Cannabigerol in Combination with Other Cannabinoid and/or Selected Terpene We further demonstrated strong synergistic effects of the minor cannabinoid, cannabigerol (CBG), on mast cell degranulation when it is combined with other cannabinoids and/or terpenes. Cannabigerol (CBG) on its own does not have significant effects on mast cell degranulation as provided in FIG. 5. However, cannabigerol (CBG) increased inhibitory effects on mast cell degranulation when it was combined with other cannabinoids and/or terpenes. For example, as highlighted in FIG. 11, the only difference between ENT 6 and ENT 9 is the presence or the absence of cannabigerol (CBG). The complex mixture comprising cannabidiol (CBD) and ENT 6 has almost no inhibitory effects, while a complex mixture comprising cannabidiol (CBD) and ENT 9 has significant inhibitory effects. The complex mixture comprising cannabidiol (CBD) and ENT 9 suppressed FcεRI ligation-induced degranulation of mast cells by 61%.

Synergistic effects of cannabigerol (CBG) were further demonstrated in combination with various concentrations of limonene or cannabidiol (CBD). As provided in FIG. 12, anti-inflammatory effects of limonene, and cannabidiol (CBD), were assessed at 11 different concentrations (x-axis: 0, 1, 5, 10, 50, 100, 500, 1000, 5000, 10000, 50000 nM) in the presence (a line with triangles and a line with circles, respectively) or absence of 10 µM cannabigerol (CBG-a line with diamonds and a line with exes, respectively). In this experiment, anti-inflammatory effects of the mixtures were based on effects on mast cell degranulation, measured using a beta-hexoseaminidase assay.

Beta-hexoseaminidase assays: Mast cells were primed with anti-DNPA IgE, and then stimulated with DNP-BSA in the presence of absence of a tested composition as described in Example 2. Mast cell culture medium was collected 60 minutes after exposure to FcεRI and incubated for 45 minutes at 37° C. 25 µl of its supernatant was removed, clarified by microcentrifugation, and transferred to a 96 well plate containing 100 µl per well 1 mM p-N-acetyl glucosamine (Sigma) in 0.05 M citrate buffer pH 4.5. After incubating the mixture for 1 hour at 37° C., the reaction was quenched by addition of 100 µl per well 0.2 M glycine, pH 9.0. Beta-hexosaminidase levels were read as OD at 405 nm.

Anti-inflammatory effects of cannabigerol were not significant when cannabigerol was applied on its own—cannabigerol suppressed FcεRI ligation-induced degranulation less than 10% even at the highest concentration tested (50 µM). However, cannabigerol demonstrated significant synergistic effects when combined with limonene or cannabidiol. When cannabigerol was added to various concentrations of limonene or cannabidiol, it significantly enhanced their anti-inflammatory effects, by shifting the dose response curve of limonene or cannabidiol to the left as shown in the graph. For example, the IC50 of anti-inflammatory responses for limonene alone was about 480 nM, but the IC50 for limonene when combined with 10 µM cannabigerol was about 100 nM (FIG. 13).

5.9.5. Example 5

Anti-Inflammatory Effects of Cannabinoid-Containing Complex Mixtures Based on Inhibition of Leukotriene C4 Release Effects of cannabinoid-containing complex mixtures on mast cell activation were also tested by measuring their effects of FcεRI ligation-induced leukotriene C4 (LTC4) release. As provided in FIG. 14, application of DNP-BSA to mast cells primed with anti-DNP IgE induces release of LTC4 from mast cells in a concentration-dependent manner. FIG. 14 shows LTC4 release (y-axis, pg/30 million cells) in response to various concentrations of DNP-BSA, ranging from 1 to 500 ng/ml. LTC4 was measured as described below.

Leukotriene C4 ELISA: Mast cell ligation of FcεRI was stimulated by addition of DNP-BSA after priming with anti-DNP IgE, in the presence or absence of a tested composition as described in Example 1. After 1 hour, supernatants from the mast cell culture were assayed for LTC4 using an EIA kit (Cayman Chemicals, Ann Arbor, Mich.) in reference to a standard curve. Color development proceeded for 45 minutes and absorbance was read at 430 nm. Results are reported as a mean (±SD) of triplicates.

LTC4 was measured in the medium after stimulation with DNP-BSA in the presence or absence of various cannabinoid-containing complex mixtures. Specifically, complex mixtures comprising cannabidiol and one of the sub-mixtures, ENT1A, ENT2, ENT3A, ENT8A or ENT9A, were tested. As presented in FIG. 15, the cannabinoid-containing complex mixtures significantly suppressed FcεRI ligation-induced LTC4 release from mast cells. The second column shows FcεRI ligation-induced LTC4 release in the presence or absence of various complex mixtures, the third column shows % LTC4 release as compared to LTC4 release in the absence of a cannabinoid-containing complex mixture (100%), and the fourth column provides % inhibition by subtracting the % LTC4 release from 100%. A cannabinoid-containing complex mixture comprising cannabidiol and ENT1A had the most profound inhibitory effect on LTC4 release—suppressing FcεRI ligation-induced LTC4 release by 73% as compared to the control.

Synergistic effects of cannabinoid-containing mixtures were also observed in this data set. In other words, when anti-inflammatory effects of cannabinoid-containing complex mixtures were predicted based on the sum of anti-inflammatory effects of their components, the predicted values were less than the actual observed anti-inflammatory effects of cannabinoid-containing complex mixtures. For example, predicted inhibitory effects of a complex mixture comprising cannabidiol, two minor cannabinoid and five selected terpenes (ENT1A) on mast cell degranulation was 57% (inhibitory effects of cannabidiol and ENT2 (8%)+ inhibitory effects of cannabidiol and ENT3A (49%)), while its actual observed effects were about 73%.

5.9.6. Example 6

Cellular and Molecular Mechanisms of the Anti-Inflammatory Effects of Cannabinoid-Containing Complex Mixtures Cannabigerol (CBG) can have anti-inflammatory effects, i.e., suppress degranulation, by either (1) suppressing a pro-secretory pathway or (2) stimulating an anti-secretory pathway, or both. Activation of $G_i$-coupled receptors, CB1 and CB2, can induce $G_i$-mediated inhibition of adenylate cyclase and subsequent decrease in intracellular cAMP concentration. Since CBG is an antagonist against CB1 and CB2, which are both expressed on RBL mast cells, inhibition of CB1 and CB2 by CBG can increase intracellular cAMP and suppress mast cell degranulation. Increase of cAMP is known to suppress degranulation in mast cells.

The CB1 and CB2 receptors can be constitutively activated by their endogenous ligands such as anandamide (arachidonoyl ethanolamide or AEA). AEA is metabolized by Fatty Acid Amide Hydrolase (FAAH) and thus, endogenous levels of AEA can be increased via inhibition of FAAH, which in turn decreases intracellular cAMP. Phosphodiesterase inhibitors such as PDEI, on the other hand, can directly elevate cAMP levels.

Experiments were conducted to test the hypothesis that CBG-mediated anti-inflammatory effects, i.e., suppression of degranulation, is by increase of intracellular cAMP and the increase of intracellular cAMP results from CBG's antagonizing effects on the interaction between AEA and CB1/2 receptors. To test this hypothesis, the ability of CBG to decrease FcεRI-induced degranulation was assessed. Mast cells were incubated with or without CBG before addition of FcεRI. An FAAH inhibitor was used as a control to increase the levels of AEA and thus saturate the CB1/2 receptors, resulting in decreased cAMP. PDEI was used as a control to directly increase the levels of intracellular cAMP. Cells were also incubated with CBD alone or CBG and CBD to assess the synergistic effects of CBD and CBG.

RBL2H3 cells were pre-incubated for 3 h at 37° C. at with (i) 10 µM FAAH inhibitor LY2183240/PF750 cocktail, (ii) 10 µM PDEI 3-isobutyl-1-methylxanthine (IBMX), or (iii) vehicle (Table 3). Vehicle or 300 nM CBG (30% of the CBG dose previously determined to cause maximal enhancement of the suppressive effect of CBD) was applied to Groups D-F and J-I, the first—one hour prior to FcεRI-induction—and the second—two hour prior to FcεRI-induction (T0, antigen), and remained throughout the course of the experiment. Vehicle was DMSO, methanol, or PBS. 10 µM CBD was additionally added to Groups D-I, 20 minutes prior to FcεRI-induction of degranulation. Cellular degranulation was measured using a beta-hexoaseaminidase assay at 1 h post-induction (T60). Replicates were done in triplicate and averaged. Degranulation of each of the groups was normalized to Row L. The outcome data presented in the column "Outcome" of Table 3 is the normalized cellular degranulation response of each averaged group. Group ABC was p<0.005 relative to Group LMN. Group GHI was p<0.005 relative to Group LMN. Row F had no significant difference relative to Row D. Row E was p<0.05 relative to Row D.

These results suggest that the combination of CBD and CBG, and the PDEI can suppress degranulation by modulating the same target, i.e., cAMP.

Next, the ability for CBG to directly regulate calcium influx was assessed. CBG is also known to be a TRPM8 antagonist. TRPM8 is an ion channel that allows entry of $Na^+$ and $Ca^+$ ions into cells after activation, and thus may play a role in calcium entry into mast cells and activation of a pro-secretory pathway. CBG-mediated suppression of cellular calcium entry may play a role in the contribution of CBG to the suppression of cellular degranulation responses.

RBL2H3 cells were washed and incubated with 0.2 µM Fluo-4 for 30 minutes at 37° C. in a standard modified Ringer's solution (145 mM NaCl, 2.8 mM KC1, 10 mM CsCl, +/−1-10 mM CaCl2, 2 mM MgCl2, 10 mM glucose, 10 mM HEPES, pH 7.4, 330 mOsm). Cells were transferred to 96-well plates at 50,000 cells/well and stimulated with 1, 10, or 50 µM CBG. 500 nM ionomycin was used as positive control to induce calcium response. Calcium signals were acquired using a Flexstation 3 (Molecular Devices, Sunnydale, USA) for 3 min. Data was analyzed using SoftMax® Pro 5 (Molecular Devices).

FIG. 16 shows the results of the intracellular calcium assay. CBG treatment resulted in a moderate increase in intracellular calcium at the highest dose tested (50 µM) but

TABLE 3

| Group | −3 h | −2 h | −1 h | −0.3 h | T0 | T60 | Outcome |
|---|---|---|---|---|---|---|---|
| A | Vehicle | vehicle | Vehicle | vehicle | vehicle | Sample | 0.06 |
| B | LY2183240/PF750 | vehicle | Vehicle | vehicle | vehicle | super- | 0.10 |
| C | IBMX | vehicle | Vehicle | vehicle | vehicle | natant | 0.06 |
| D | Vehicle | CBG | CBG | CBD | Antigen | and | 0.31 |
| E | LY2183240/PF750 | CBG | CBG | CBD | Antigen | assay | 0.61 |
| F | IBMX | CBG | CBG | CBD | Antigen | | 0.33 |
| G | Vehicle | vehicle | vehicle | CBD | Antigen | | 0.54 |
| H | LY2183240/PF750 | vehicle | vehicle | CBD | Antigen | | 0.56 |
| I | IBMX | vehicle | vehicle | CBD | Antigen | | 0.32 |
| 1 | Vehicle | CBG | CBG | vehicle | Antigen | | 0.98 |
| K | LY2183240/PF750 | CBG | CBG | vehicle | Antigen | | 0.92 |
| I | IBMX | CBG | CBG | vehicle | Antigen | | 0.28 |
| L | Vehicle | vehicle | vehicle | vehicle | Antigen | | 1.0 |
| M | LY2183240/PF750 | vehicle | vehicle | vehicle | Antigen | | 1.02 |
| N | IBMX | vehicle | vehicle | vehicle | Antigen | | 0.34 |

Higher "outcome" numbers indicate increased cellular degranulation after FcεRI-induction. IBMX alone resulted in a 3-fold reduction of FcεRI-induced degranulation (Row N, 0.34), confirming that increased cAMP by IBMX can suppress degranulation. Addition of CBG alone did not reduce degranulation (Row J, 0.98 compared to Row L, 1.0; and Row K, 0.92 compared to Row M, 1.02). However, CBD alone did suppress degranulation (Row G, 0.54 compared to Row L, 1.0; and Row H, 0.56 compared to Row M, 1.02). Interestingly, the addition of CBG and CBD had a synergistic effect on the inhibition of cell degranulation, as the combination resulted in lower degranulation than CBD alone (Row D, 0.31 compared to Row G, 0.54). This demonstrates that although CBG alone may not be sufficient to directly suppress cell degranulation, the combination of CBD and CBG has a synergistic effect and results in greater suppression of degranulation than CBD alone.

Furthermore, the combination of CBD and CBG resulted in the same degranulation inhibition as the PDEI cocktail (Row D, 0.31 compared to Row F, 0.33 and Row N, 0.34), and the combination of CBD and CBG did not additionally suppress degranulation when applied to the cells treated with the PDEI cocktail (Row N, 0.34 compared to Row F, 0.33).

did not significantly alter the intracellular calcium at the lower doses (1 and 10 µM). Thus, suppression of calcium influx is likely not the mechanism by which CBG suppresses cell degranulation.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

The present disclosure provides, inter alia, compositions of cannabinoid-containing complex mixtures capable of inhibiting mast cell degranulation. The present disclosure also provides methods of treating immune disorders by administering the cannabinoid-containing complex mixtures. While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A method of treating Mast Cell Activation syndrome, the method comprising:
   administering to a subject with Mast Cell Activation syndrome an effective amount of a pharmaceutical composition comprising:
   cannabidiol (CBD);
   a first minor cannabinoid that is cannabigerol (CBG);
   a second minor cannabinoid that is cannabichromene (CBC);
   a third minor cannabinoid that is cannabidivarin (CBDV);
   a first terpene that is limonene;
   a second terpene that is linalool; and
   a pharmaceutically acceptable carrier or diluent,
   wherein the pharmaceutical composition is free of delta-9 tetrahydrocannabinol (THC).

2. The method of claim 1, wherein the pharmaceutical composition is administered orally, by inhalation, by buccal administration, by sublingual administration, by injection, or by topical application.

3. The method of claim 2, wherein the pharmaceutical composition is administered orally.

4. The method of claim 2, wherein the pharmaceutical composition is administered by inhalation.

5. The method of claim 2, wherein the pharmaceutical composition is administered by injection.

6. The method of claim 1, wherein the pharmaceutical composition is administered once a day, 2-4 times a day, 2-4 times a week, once a week, or once every two weeks.

7. The method of claim 1, wherein the cannabidiol (CBD) is administered in an amount of less than 1 gram per dose.

8. The method of claim 1, wherein the cannabidiol (CBD) is administered in an amount of less than 500 milligrams per dose.

9. The method of claim 1, wherein the cannabidiol (CBD) is administered in an amount of less than 100 milligrams per dose.

10. The method of claim 1, wherein the cannabidiol (CBD) is administered in an amount of less than 10 milligrams per dose.

11. The method of claim 1, wherein the subject is human.

* * * * *